(12) United States Patent
Kauss et al.

(10) Patent No.: US 7,550,482 B2
(45) Date of Patent: Jun. 23, 2009

(54) TETRAHYDROQUINOLONES AND THEIR USE AS MODULATORS OF METABOTROPIC GLUTAMATE RECEPTORS

(75) Inventors: Valerjans Kauss, Riga (LV); Ieva Jaunzeme, Riga (LV); Aigars Jirgensons, Riga (LV); Ivars Kalvinsh, Salaspils (LV); Maksims Vanejevs, Riga (LV); Markus Henrich, Wetzlar (DE); Wojciech Danysz, Nidderau (DE); Claudia Jatzke, Frankfurt am Main (DE); Christopher Graham Raphael Parsons, Nidderau (DE); Tanja Weil, Heidelberg (DE)

(73) Assignee: Merz Pharma GmbH & Co. KGAA, Frankfurt Main (DE)

( * ) Notice: Subject to any disclaimer, the term of this patent is extended or adjusted under 35 U.S.C. 154(b) by 546 days.

(21) Appl. No.: 11/210,569

(22) Filed: Aug. 24, 2005

(65) Prior Publication Data
US 2005/0288284 A1    Dec. 29, 2005

Related U.S. Application Data

(63) Continuation-in-part of application No. 11/066,899, filed on Feb. 25, 2005.

(60) Provisional application No. 60/548,788, filed on Feb. 27, 2004.

(51) Int. Cl.
C07D 215/38    (2006.01)
A61K 31/44     (2006.01)

(52) U.S. Cl. .................. 514/313; 546/177; 546/178

(58) Field of Classification Search ............ 546/177, 546/178; 514/313
See application file for complete search history.

(56) References Cited

U.S. PATENT DOCUMENTS

| | | | | |
|---|---|---|---|---|
| 6,133,303 | A * | 10/2000 | Bikker et al. | 514/399 |
| 6,265,422 | B1 * | 7/2001 | Bikker et al. | 514/341 |
| 6,472,408 | B1 | 10/2002 | Carlier et al. | |
| 6,528,535 | B2 * | 3/2003 | Bikker et al. | 514/398 |

FOREIGN PATENT DOCUMENTS

| | | |
|---|---|---|
| DE | 2001572 | 7/1971 |
| DE | 2449030 | 5/1976 |
| FR | 2287224 | 5/1976 |
| WO | WO 88/02251 | 4/1988 |
| WO | WO 02/28837 | 4/2002 |
| WO | WO 03/082350 | 10/2003 |

OTHER PUBLICATIONS

International Search Report for International Application No. PCT/GB2005/00717, Sep. 16, 2005.
Dostenko, et al., *Russ. Chem. Bull., Int. Ed.*, 2002, 51, 1556-1561.
Pitts, et al., *Biorg. Med. Chem. Lett.*, 1998, 8, 307-312.
Schroeder, et al., *Eur. J. Med. Chem.—Chimica Therapeutica*, 1979, 14, 309-315.
Shanazarov, et al., *Khimiya Geterotsiklicheskikh Soedinenii*, 1991, 1, 86-92.
Haas, et al., *J. Heterocyclic Chem.*, 1981, 18, 619-622.
Schoepp, et al., *Neuropharmacology*, 1999, 38, 1431-1476.
Roedig, et al., *Chem. Ber.*, 1958, 91, 330-339.
Roedig, et al., *Chem. Ber.*, 1960, 93, 2294-2300.
Stankevich et al., *Chem. Heterocycl. Compd.* (Engl. Transl.), 1966, 2, 440-442; translated from *Khim. Geterotsikl. Soedin.*, 1966, 2, 583-585.
Gudrinietse et al.; *Latv. PSR Zinat.Akad.Vestis Khim.Ser.*; 1972; 622; *Chem. Abstr.*; 78; 29581m; 1973.
Yukhnevich et al *Latv. PSR Zinat. Akad. Vestis Khim. Ser.*; 1973; 699; *Chem. Abstr.*; 80; 82603n; 1974.
Junek, et al., *Z. Naturforsch. B*, 1970, 25, 1423-1426.
Katsuri, et al., *Tetrahedron*, 1975, 31, 527-531.
Albrecht, et al., *Arch. Pharm.*, 1975, 308, 588-594.
Roth, et al., *Arch. Pharm.*, 1977, 310, 48-55.
Bennett, et al., *J. Heterocycl. Chem.*, 1979, 16, 633-635.
Reimann, et al., *Arch. Pharm.*, 1985, 318, 871-878.
Reimann, et al., *Arch. Pharm.*, 1985, 318, 1105-1115.
Nitta, et al., *Bull. Chem. Soc. Jpn.*, 1990, 63, 932-934.
Murogova, et al., *Pharm.Chem.J.* (Engl. Transl.), 1990, 24, 633-638.
Gatta, et al., *Heterocycles*, 1992, 34, 991-1004.
Molina, et al., *Tetrahedron*, 1995, 51, 1265-1276.
Fink, et al.; *J. Med. Chem.*, 1995, 38, 3645-3651.
Miyabara, et al., *Heterocycles*, 1999, 51, 983-988.
Pyrko, *Chem. Heterocycl. Compd.* (Engl. Transl.), 1999, 35, 688-694.
Fukumoto, et al., *J. Med. Chem.* 2002, 45, 3009-3021.
Okada, et al., *Heterocycles*, 1997, 46, 129-132.
Lopez-Calle, et al., *Liebigs Ann. Org. Bioorg. Chem.*, 1996, 11, 1855-1866.
Carlier, et al., *Angew. Chem. Int. Ed. Eng.*, 2000, 112, 1845-1847.
Kantlehner, et al., *J. Prakt. Chem. / Chem.-Ztg.*, 1998, 340, 408-423.
International Search Report for International Application No. PCT/GB2005/003285, May 12, 2006.
Bruno et al., *Neuropharmacology*, 2000, 39, 2223-30.
O'Leary et al., *Br. J. Pharmacol.*, 2000, 131, 1429-3.
Battaglia et al., *J. Neurosci.* 2001, 2, 2135-41.
Rao et al., *Neurosci. Lett.*, 2000, 293, 1-4.
Popoli et al., *J. Neurochem.*, 2004, 89, 1479-89.
Jaeschke et al., *Expert. Opin. Ther. Patents*, 2008, 18, 123-142.
Feligioni et al., *J. Neurosci.*, 2003, 23, 6810-8.
Cowen, et al., *J. Pharmacol. Exp. Ther.*, 2005, 315, 590-600.
Vengeliene, et al., *Neuropharmacology*, 2005, 48, 822-829.

(Continued)

Primary Examiner—D. Margaret Seaman
(74) Attorney, Agent, or Firm—Hueschen and Sage

(57) ABSTRACT

The invention relates to ethynyl-substituted tetrahydroquinolinone derivatives as well as their pharmaceutically acceptable salts. The invention further relates to a process for the preparation of such compounds. The compounds of the invention are group I mGluR modulators and are therefore useful for the control and prevention of acute and/or chronic neurological disorders.

11 Claims, No Drawings

OTHER PUBLICATIONS

Bachteler, et al., *Neuropsychopharmacology*, 2005, 30, 1104-1110.
Aronica et al., *Neuroscience*, 2001, 105, 509-20.
Ma, et al., *Neuroscience*, 2006, 143, 95-104.
Shi et al., *J. Pharmacol. Exp. Ther.*, 2003 305, 131-42.
Bruno et al., *J. Cereb. Blood Flow Metab.*, 2001, 21, 1013-33.
Oka, et al., *Acta Neuropathol.*, 1999, 97, 275-278.
Balschun et al., *Neuroscience*, 2006, 142, 691-702.
Liu, et al., *J. Neurochem.*, 2005, 95, 1363-72.
Aaononsen, et al., *J. Pharmacol. Exp. Ther.*, 1999, 248, 1034-1038.
Spooren, et al., *Eur. J. Pharmacol.*, 2000, 406, 403-10.
Schultz, et al., *Neuropharmacology*, 2001, 41, 1-7.
Tatarczynska, et al., *Br. J. Pharmacol.*, 2001, 132, 1423-30.
Spooren, et al., *Eur. J. Pharmacol.*, 2002, 435, 161-70.
Brodkin, et al., *Pharmacol. Biochem. Behav.*, 2002, 73, 359-66.
Cosford, et al., *J. Med. Chem.*, 2003, 46, 204-6.
Pietraszek, et al., *Eur. J. Pharmacol.*, 2005, 514, 25-34.
Gravius, et al., *Neuropharmacology*, 2006, 51, 1146-1155.
Varty, et al., *Psychopharmacology (Berl)*, 2005, 179, 207-17.
Ballard, et al., *Psychopharmacology (Berl)*, 2005, 179, 218-29.
Huber, et al., *Proc Natl Acad Sci USA*, 2002, 99, 7746-50.
Kenny, et al., *An. N Y Acad Sci*, 2003, 1003, 415-418.
Chiamulera et al., *Nat Neurosci*, 2001, 4, 873-4.
Belozertseva, et al., *Eur. Neuropsychopharmacol.*, 2007, 17, 172-179.
Palucha, et al., *Pharmacol. Biochem. Behav.*, 2005, 81, 901-6.
Li, et al., *J. Pharmacol. Exp. Ther.*, 2006, 319, 254-9.
Pilc, et al., *Neuropharmacology*, 2002, 43, 181-7.
Storto, et al., *Mol. Pharmacol.*, 2006, 69, 1234-1241.
Tizzano, et al., *Neuropharmacology*, 1995, 34, 1063-1067.
Camon, et al., *J. Neurosci. Res.*, 1998, 51, 339-348.
Barton, et al., *Epilepsy Res.*, 2003, 56, 17-26.
Chapman, et al., *Neuropharmacology*, 2000, 39, 1567-1574.
Frisby, et al., *Gastroenterology*, 2005, 129, 995-1004.
Jensen, et al., *Eur. J. Pharmacol.*, 2005, 519, 154-7.
Frati, et al., *J Cell Physiol*, 2000, 183, 364-72.
Aronica, et al., *Eur. J. Neurosci.*, 2003, 17, 2106-18.
Ye, et al., *Cancer Res*, 1999, 59, 4383-9.
Albasanz, et al., *Eur. J. Pharmacol.*, 1997, 326, 85-91.
Park, et al., *Oncol Rep*, 2007, 17, 81-7.
Movsesyan et al., *J. Pharmacol. Exp. Ther.*, 2001, 296, 41-7.
Lea et al., *Pharmacol. Biochem. Behav.*, 2002, 73, 287-98.
Gong et al., *J. Neurotrauma*, 1999, 16, 893-902.
Llansola et al., *Neuroscience*, 2005, 133, 185-91.
Canales et al., *Neurobiol Dis*, 2003, 14, 380-90.
Orlando, et al., *Neurosci. Lett.*, 1995, 202, 109-12.
Addex—http://www.addexpharma.com/press-releases-old/news-releases/20-april-2007/.
Popik, et al., *Neuropharmacology*, 2002, 43, 1210-7.
Palucha et al., *Pol. J. Pharmacol.*, 2004, 56, 863-6.
Kotlinska, et al., *Eur. J. Pharmacol.*, 2007, 558, 113-8.
Kozela, et al., *Psychopharmacology (Berl)*, 2003, 165, 245-51.
Narita, et al., *J. Neurochem.*, 2005, 94, 1297-305.
Geurts et al., *Brain*, 2003, 126, 1755-66.
Paterson, et al., *Psychopharmacology (Berl)*, 2005, 179, 255-61.
Bespalov, et al., *Neuropharmacology*, 2005, 49 Suppl, 167-178.
Bisaga et al., *Eur. Neuropsychopharmacol.*, 2008, published online #42677.
Bradbury, et al., *J. Pharmacol. Exp. Ther.*, 2005, 313, 395-402.
Karim, et al., *J. Neurosci.*, 2001, 21, 3771-9.
Urban, et al., *Neuropharmacology*, 2003, 44, 983-93.
Fisher, et al., *Pharmacol. Biochem. Behav.*, 2002, 73, 411-8.
Sevostianova, et al., *Neuropharmacology*, 2006, 51, 623-630.
Hudson, et al., *J. Neurosci.*, 2002, 22, 2660-8.
Mills, et al., *J. Neurotrauma*, 2002, 19, 23-42.
Walker, et al., *Neuropharmacology*, 2001, 40, 1-9.
Walker, et al., *Neuropharmacology*, 2001, 40, 10-9.
Ossowska, et al., *Neuropharmacology*, 2001, 41, 413-20.
Ossowska, et al. *Neuropharmacology*, 2005, 49, 447-455.
Breysse, et al., *J. Neurosci.*, 2002, 22, 5669-78.
Breysse, et al., *J. Neurosci.*, 2003, 23, 8302-9.
Turle-Lorenzo, et al., *Psychopharmacology (Berl)*, 2005, 179, 117-127.
Golembiowska, et al., *Neuropharmacology*, 2003, 45, 484-492.
Battaglia, et al., *J. Neurosci.*, 2002, 22, 2135-41.
Armentero, et al., *Neurobiol Dis*, 2006, 22, 1-9.
Dekundy, et al., *Brain Res. Bull.*, 2006, 69, 318-326.
Mela, et al., *J. Neurochem.*, 2007, 101, 483-97.
Kinney, et al., *J. Pharmacol. Exp. Ther.*, 2005, 313, 199-206.
Mills, et al., *J. Neurochem.*, 2001, 79, 835-48.
Szydlowska, et al., *Eur. J. Pharmacol.*, 2007, 554, 18-29.

\* cited by examiner

TETRAHYDROQUINOLONES AND THEIR USE AS MODULATORS OF METABOTROPIC GLUTAMATE RECEPTORS

FIELD OF THE INVENTION

The present invention is concerned with novel metabotropic glutamate receptor (mGluR) modulators, methods for their synthesis and the treatment and/or prevention of neurological disorders by administration of such substances.

BACKGROUND OF THE INVENTION

Neuronal stimuli are transmitted by the central nervous system (CNS) through the interaction of a neurotransmitter released by a neuron, which neurotransmitter has a specific effect on a neuroreceptor of another neuron.

L-glutamic acid is considered to be the major excitatory neurotransmitter in the mammalian CNS, consequently playing a critical role in a large number of physiological processes. Glutamate-dependent stimulus receptors are divided into two main groups. The first group comprises ligand-controlled ion channels whereas the second comprises metabotropic glutamate receptors (mGluR). Metabotropic glutamate receptors are a subfamily of G-protein-coupled receptors (GPCR). There is increasing evidence for a peripheral role of both ionotropic and metabotropic glutamate receptors outside of the CNS e.g., in chronic pain states.

At present, eight different members of these mGluRs are known. On the basis of structural parameters such as sequence homology, the second messenger system utilized by these receptors and their different affinity to low-molecular weight compounds, these eight receptors can be divided into three groups: mGluR1 and mGluR5 belong to group I which couple to phospholipase C and their activation leads to intracellular calcium-ion mobilization. Both mGluR2 and mGluR3 belong to group II and mGluR4, mGluR6, mGluR7 and mGluR8 belong to group III, which couple to adenyl cyclase with their activation causing a reduction in second messenger cAMP and as such a dampening of the neuronal activity.

Group I mGluR modulators have been shown to modulate the effects of the presynaptically released neurotransmitter glutamate via postsynaptic mechanisms. Moreover, as these modulators can be both positive and/or negative Group I mGluR modulators, such modulators may increase or inhibit the effects of these metabotropic receptors. Since a variety of pathophysiological processes and disease states affecting the CNS are thought to be related to abnormal glutamate neurotransmission and group I mGluRs are shown to be expressed in several areas of the CNS, modulators of these receptors could be therapeutically beneficial in the treatment of CNS diseases.

Therefore, group I mGluR modulators may be administered to provide neuroprotection in acute and chronic pathological conditions such as: AIDS-related dementia, Alzheimer's disease, Creutzfeld-Jakob's syndrome, bovine spongiform encephalopathy (BSE) or other prion related infections, diseases involving mitochondrial dysfunction, diseases involving β-amyloid and/or tauopathy such as Down's syndrome, hepatic encephalopathy, Huntington's disease, motor neuron diseases such as amyotrophic lateral sclerosis (ALS), multiple sclerosis (MS), olivoponto-cerebellar atrophy, post-operative cognitive deficit (POCD), Parkinson's disease, Parkinson's dementia, mild cognitive impairment, dementia pugilisitca, vascular and frontal lobe dementia, cognitive impairment, eye injuries or diseases (e.g. glaucoma, retinopathy, macular degeneration), head and spinal cord injuries/trauma, hypoglycaemia, hypoxia (e.g. perinatal), ischaemia (e.g. resulting from cardiac arrest, stroke, bypass operations or transplants), convulsions, glioma and other tumours, inner ear insult (e.g. in tinnitus, sound or drug-induced), L-dopa-induced and tardive dyskinesias.

Other indications in this context include a symptomatological effect on the following conditions: addiction (nicotine, alcohol, opiate, cocaine, amphetamine obesity and others), amyotrophic lateral sclerosis (ALS), anxiety and panic disorders, attention deficit hyperactivity disorder (ADHD), restless leg syndrome and hyperactive children, autism, convulsions/epilepsy, dementia (e.g. in Alzheimer's disease, Korsakoff syndrome, vascular dementia, HIV infections), major depressive disorder or depression (including that resulting from Borna virus infection) and bipolar manic-depressive disorder, drug tolerance e.g. to opioids, movement disorders, dystonia, dyskinesia (e.g. L-Dopa-induced, tardive dyskinesia or in Huntington's disease), fragile-X syndrome, Huntington's chorea, irritable bowel syndrome (IBS), migraine, multiple sclerosis, muscle spasms, pain (chronic and acute, e.g. inflammatory pain, neuropathic pain, allodynia, hyperalgesia, nociceptive pain), Parkinson's disease, post traumatic stress disorder, schizophrenia (positive and negative symptoms), spasticity, tinnitus, Tourette's syndrome, urinary incontinence and vomiting, pruritic conditions (e.g. pruritis), sleep disorders, micturition disorders, neuromuscular disorder in the lower urinary tract, gastroesophageal reflux disease (GERD), lower esophageal sphincter (LES), functional gastrointestinal disorders, dyspepsia, regurgitation, respiratory tract infection, bulimia nervosa, chronic laryngitis, asthma (e.g. reflux-related asthma), lung disease, eating disorders, obesity and obesity-related disorders.

Yet further indications for Group I mGluR modulators include those indications wherein a particular condition does not necessarily exist but wherein a particular physiological parameter may be improved through administration of the instant compounds, for example cognitive enhancement.

Positive modulators may be particularly useful in the treatment of positive and negative symptoms in schizophrenia and cognitive deficits in various forms of dementia and mild cognitive impairment.

Among the Group I mGluR modulators, those which exhibit a modulatory effect on mGluR5 receptors and thus may affect conditions or diseases associated with the function of those mGluR5 receptors are of particular interest. In addition to the utility of mGluR5 modulators in preventing and/or treating the conditions and/or diseases mentioned above, mGluR5 positive modulators or agonists may be particularly useful for preventing and/or treating conditions or diseases that are associated with an insufficient stimulation or activity of mGluR5 receptors. mGluR5 modulators and especially mGluR5 positive modulators or agonists may be particularly useful for preventing and/or treating addiction, neuropathic pain, L-dopa-induced and tardive dyskinesias, ALS, fragile-X syndrome, Parkinson's disease, anxiety disorders, epilepsy, positive and/or negative symptoms of schizophrenia, cognitive impairment, or for cognitive enhancement and neuroprotection.

THE PRESENT INVENTION

We have determined that certain ethynyl-substituted tetrahydroquinolones are Group I mGluR modulators and in particular mGluR5 modulators. Therefore, these substances may be therapeutically beneficial in the treatment of conditions which involve abnormal glutamate neurotransmission or in which modulation of Group I mGluR receptors results in therapeutic benefit. These substances are preferably administered in the form of a pharmaceutical composition, wherein they are present together with one or more pharmaceutically acceptable diluents, carriers, or excipients.

OBJECTS OF THE INVENTION

It is an object of the present invention to provide novel pharmaceutical compounds which are tetrahydroquinolone Group I mGluR modulators and pharmaceutical compositions thereof. It is a further object of the invention to provide a novel method of treating, eliminating, alleviating, palliating, or ameliorating undesirable CNS disorders which involve abnormal glutamate neurotransmission by employing a compound of the invention or a pharmaceutical composition containing the same. An additional object of the invention is the provision of a process for producing the tetrahydroquinolone active principles. Yet additional objects will become apparent hereinafter, and still further objects will be apparent to one skilled in the art.

SUMMARY OF THE INVENTION

What we therefore believe to be comprised by our invention may be summarized inter alia in the following words:

A compound of Formula I wherein $R^1$ represents aryl or heteroaryl;

$R^2$ and $R^3$, which may be the same or different, represent hydrogen or $C_{1-6}$alkyl;

$R^4$ and $R^5$, which may be the same or different, represent hydrogen or $C_{1-6}$alkyl;

it being understood that:

aryl represents an unsubstituted phenyl ring or a phenyl ring that is substituted with 1, 2, 3, 4 or 5 substituents, that may be the same or different, which substituents are selected from $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$alkylamino, N-cyclo$C_{3-12}$alkyl-N-$C_{1-6}$alkylamino, azetidinyl, pyrrolidinyl, piperidinyl, morpholinyl, 4-$C_{1-6}$alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;

heteroaryl represents a (hetero)aromatic 5-, 6- or 7-membered ring having from 1 to 4 heteroatoms, said heteroatoms being independently selected from oxygen, nitrogen and sulfur, wherein said ring is unsubstituted or substituted with 1, 2 or 3 substituents, that may be the same or different, which substituents are selected from $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$alkylamino, N-cyclo$C_{3-12}$alkyl-N-$C_{1-6}$alkylamino, azetidinyl, pyrrolidinyl, piperidinyl, morpholinyl, 4-$C_{1-6}$alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;

and optical isomers, pharmaceutically acceptable salts, hydrates, solvates, and polymorphs thereof.

Such a compound of Formula I, wherein
$R^2$ and $R^3$, which may be the same or different, represent methyl, ethyl, n-propyl, 2-propyl, n-butyl, tert-butyl and
$R^4$ and $R^5$ represent hydrogen;

Such a compound of Formula I, wherein
$R^2$ and $R^3$ represent hydrogen and
$R^4$ and $R^5$, which may be the same or different, represent methyl, ethyl, n-propyl, 2-propyl, n-butyl, tert-butyl;

Such a compound of Formula I, wherein
$R^2$, $R^3$, $R^4$ and $R^5$, which may be the same or different, represent hydrogen, methyl or ethyl;

Such a compound of Formula I, wherein
$R^1$ represents aryl;
it being understood that:
aryl represents unsubstituted phenyl or phenyl that is mono- or di-substituted with the same or different substituents that are selected from methyl, ethyl, n-propyl, 2-propyl, n-butyl, tert-butyl, hydroxyl, methoxy, ethoxy, n-propoxy, iso-propoxy, n-butoxy, tert-butoxy, $CF_3$, $CH_2F$, $CH_2F$, $C_2F_5$, $OCF_3$, $OC_2F_5$, F, Cl, Br, CN, piperidinyl, morpholinyl, tetrazolyl, oxazolyl, furyl, thiophenyl, pyrrolyl, isoxazolyl, thiazolyl, imidazolyl, oxadiazolyl, pyridinyl, pyrimidyl, phenyl;

Such a compound of Formula I, wherein aryl represents unsubstituted phenyl or a phenyl ring that is mono- or di-substituted with the substituent(s) in the meta-position.

Such a compound of Formula I, wherein the phenyl ring is di-substituted in the meta-position and the substituents are different.

Such a compound of Formula I, wherein the substituents are selected from F, CN, pyridinyl, tetrazolyl and unsubstituted phenyl.

Such a compound of Formula I, wherein
$R^1$ represents heteroaryl;
it being understood that:
heteroaryl represents pyridin-2-yl, pyridin-3-yl, pyridin-4-yl, oxazol-5-yl, thiazol-5-yl, wherein each of these rings may be unsubstituted or mono or di-substituted with phenyl, methyl, ethyl, n-propyl, 2-propyl, n-butyl, tert-butyl, hydroxyl, methoxy, ethoxy, n-propoxy, iso-propoxy, n-butoxy, tert-butoxy, $CF_3$, $CH_2F$, $CH_2F$, $C_2F_5$, $OCF_3$, $OC_2F_5$, F, Cl, Br, CN, piperidinyl, morpholinyl, tetrazolyl, oxazolyl, furyl, thiophenyl, isoxazolyl, thiazolyl, imidazolyl, oxadiazolyl, pyridinyl, pyrimidyl;

Such a compound of Formula I, wherein heteroaryl represents unsubstituted heteroaryl or an heteroaryl ring that is mono- or di-substituted with the substituent(s) in the meta-position.

Such a compound of Formula I, wherein the heteroaryl ring is di-substituted in the meta-position and the substituents are different.

Such a compound of Formula I, wherein the substituents are selected from F, CN, pyridinyl, tetrazolyl and unsubstituted phenyl.

Moreover, a method-of-treating a living animal, including a human, for a condition or a disease associated with abnormal glutamate neurotransmission or in which modulation of Group I mGluR receptors results in therapeutic benefit comprising the step of administering to the living animal, including a human, an amount of a Group I mGluR modulator selected from those of Formula I

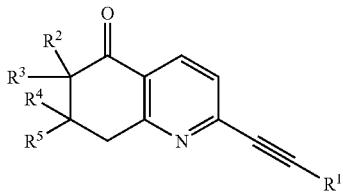

wherein
$R^1$ represents aryl or heteroaryl;
$R^2$ and $R^3$, which may be the same or different, represent hydrogen or $C_{1-6}$alkyl;
$R^4$ and $R^5$, which may be the same or different, represent hydrogen or $C_{1-6}$alkyl;
it being understood that:
aryl represents an unsubstituted phenyl ring or a phenyl ring that is substituted with 1, 2, 3, 4 or 5 substituents, that may be the same or different, which substituents are selected from $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$ alkyl, hydroxyl, F, Cl, Br, I, CN, nitro, di-$C_{1-6}$alkylamino, N-cyclo$C_{3-12}$alkyl-N-$C_{1-6}$alkylamino, azetidinyl, pyrrolidinyl, piperidinyl, morpholinyl, 4-$C_{1-6}$alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
heteroaryl represents a (hetero)aromatic 5-, 6- or 7-membered ring having from 1 to 4 heteroatoms, said heteroatoms being independently selected from oxygen, nitrogen and sulfur, wherein said ring is unsubstituted or substituted with 1, 2 or 3 substituents, that may be the same or different, which substituents are selected from the group consisting of $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$ alkylamino, N-cyclo$C_{3-12}$alkyl-N-$C_{1-6}$alkylamino, azetidinyl, pyrrolidinyl, piperidinyl, morpholinyl, 4-$C_{1-6}$ alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
or optical isomers, pharmaceutically acceptable salts, hydrates, solvates, and polymorphs thereof;
which is effective for alleviation of the condition or disease or for enhancing cognition.

Such a method wherein the condition associated with abnormal glutamate neurotransmission, or wherein modulation of mGluR receptors results in therapeutic benefit, is selected from: AIDS-related dementia, Alzheimer's disease, Creutzfeld-Jakob's syndrome, bovine spongiform encephalopathy (BSE) or other prion related infections, diseases involving mitochondrial dysfunction, diseases involving β-amyloid and/or tauopathy such as Down's syndrome, hepatic encephalopathy, Huntington's disease, motor neuron diseases such as amyotrophic lateral sclerosis (ALS), multiple sclerosis (MS), olivoponto-cerebellar atrophy, post-operative cognitive deficit (POCD), Parkinson's disease, Parkinson's dementia, mild cognitive impairment, dementia pugilisitca, vascular and frontal lobe dementia, cognitive impairment, eye injuries or diseases (e.g. glaucoma, retinopathy, macular degeneration), head and spinal cord injuries/trauma, hypoglycaemia, hypoxia (e.g. perinatal), ischaemia (e.g. resulting from cardiac arrest, stroke, bypass operations or transplants), convulsions, glioma and other tumours, inner ear insult (e.g. in tinnitus, sound or drug-induced), L-dopa-induced and tardive dyskinesias, addiction (nicotine, alcohol, opiate, cocaine, amphetamine obesity and others), anxiety and panic disorders, attention deficit hyperactivity disorder (ADHD), restless leg syndrome, hyperactive children, autism, convulsions/ epilepsy, dementia (e.g. in Alzheimer's disease, Korsakoff syndrome, vascular dementia, HIV infections), major depressive disorder or depression (including that resulting from Borna virus infection) and bipolar manic-depressive disorder, drug tolerance e.g. to opioids, movement disorders, dystonia, dyskinesia (e.g. L-Dopa-induced, tardive dyskinesia or in Huntington's disease), fragile-X syndrome, Huntington's chorea, irritable bowel syndrome (IBS), migraine, multiple sclerosis, muscle spasms, pain (chronic and acute, e.g. inflammatory pain, neuropathic pain, allodynia, hyperalgesia, nociceptive pain), Parkinson's disease, post traumatic stress disorder, schizophrenia (positive and negative symptoms), spasticity, Tourette's syndrome, urinary incontinence and vomiting, pruritic conditions (e.g. pruritis), sleep disorders, micturition disorders, neuromuscular disorder in the lower urinary tract, gastroesophageal reflux disease (GERD), lower esophageal sphincter (LES) disease, functional gastrointestinal disorders, dyspepsia, regurgitation, respiratory tract infection, bulimia nervosa, chronic laryngitis, asthma (e.g. reflux-related asthma), lung disease, eating disorders, obesity and obesity-related disorders, agoraphobia, generalized anxiety disorder, obsessive-compulsive disorder, panic disorder, posttraumatic stress disorder, social phobia, substance-induced anxiety disorder, delusional disorder, schizoaffective disorder, schizophreniform disorder, substance-induced psychotic disorder, delirium, or for cognitive enhancement or neuroprotection.

Such a method wherein the compound is administered in the form of a pharmaceutical composition thereof comprising the compound of Formula I in combination with one or more pharmaceutically-acceptable diluents, excipients, or carriers.

Further, the use of at least one compound of Formula I

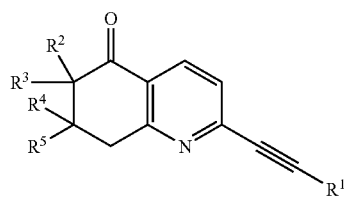

wherein
$R^1$ represents aryl or heteroaryl;
$R^2$ and $R^3$, which may be the same or different, represent hydrogen or $C_{1-6}$alkyl;
$R^4$ and $R^5$, which may be the same or different, represent hydrogen or $C_{1-6}$alkyl;

it being understood that:
aryl represents an unsubstituted phenyl ring or a phenyl ring that is substituted with 1, 2, 3, 4 or 5 substituents, that may be the same or different, which substituents are selected from $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$ alkyl, hydroxyl, F, Cl, Br, I, CN, nitro, di-$C_{1-6}$alkylamino, N-cyclo$C_{3-12}$alkyl-N-$C_{1-6}$alkylamino, azetidinyl, pyrrolidinyl, piperidinyl, morpholinyl, 4-$C_{1-6}$alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
heteroaryl represents a (hetero)aromatic 5-, 6- or 7-membered ring having from 1 to 4 heteroatoms, said heteroatoms being independently selected from oxygen, nitrogen and sulfur, wherein said ring is unsubstituted or substituted with 1, 2 or 3 substituents, that may be the same or different, which substituents are selected from the group consisting of $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$ alkylamino, N-cyclo$C_{3-12}$alkyl-N $C_{1-6}$alkylamino, azetidinyl, pyrrolidinyl, piperidinyl, morpholinyl, 4-$C_{1-6}$ alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
and optical isomers, pharmaceutically acceptable salts, hydrates, solvates, and polymorphs thereof;
for the manufacturing of a medicament for the prevention and/or treatment of a condition or disease in an animal including a human being which condition or disease is affected or facilitated by the modulatory effect of Group I mGluR1 modulators and in particular of mGluR5 modulators.

The compounds of Formula I used according to the present invention for the manufacturing of a medicament have been found to be modulators of Group I mGluR receptors. In particular, these compounds are modulators of mGluR5 receptors. Surprisingly it has been found that they show at least partially agonistic or positive modulatory effects on the mGluR5 receptors.

Consequently, one aspect of the present invention is the use of one or more compounds of formula I

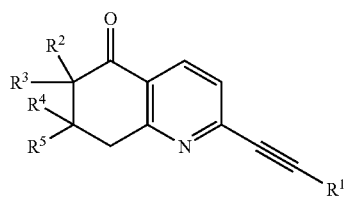

I wherein
$R^1$ represents aryl or heteroaryl;
$R^2$ and $R^3$, which may be the same or different, represent hydrogen or $C_{1-6}$alkyl;
$R^4$ and $R^5$, which may be the same or different, represent hydrogen or $C_{1-6}$alkyl;

it being understood that:
aryl represents an unsubstituted phenyl ring or a phenyl ring that is substituted with 1, 2, 3, 4 or 5 substituents, that may be the same or different, which substituents are selected from $C_{1-6}$alkyl, which is optionally substituted with one or more fluorine, chlorine or bromine atoms, $C_{1-6}$ alkoxy, which is optionally substituted with one or more fluorine, chlorine or bromine atoms, cyclo$C_{3-12}$ alkyl, hydroxyl, F, Cl, Br, I, CN, nitro, di-$C_{1-6}$alkylamino, N-cyclo$C_{3-12}$alkyl-N-$C_{1-6}$alkylamino, azetidinyl, pyrrolidinyl, piperidinyl, morpholinyl, 4-$C_{1-6}$alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
heteroaryl represents a (hetero)aromatic 5-, 6- or 7-membered ring having from 1 to 4 heteroatoms, said heteroatoms being independently selected from oxygen, nitrogen and sulfur, wherein said ring is unsubstituted or substituted with 1, 2 or 3 substituents, that may be the same or different, which substituents are selected from the group consisting of $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$ alkylamino, N-cyclo$C_{3-12}$alkyl-N- $C_{1-6}$alkylamino, azetidinyl, pyrrolidinyl, piperidinyl, morpholinyl, 4-$C_{1-6}$ alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
and optical isomers, pharmaceutically acceptable salts, hydrates, solvates, and polymorphs thereof;
for the manufacturing of a medicament for the prevention and/or treatment of AIDS-related dementia, Alzheimer's disease, Creutzfeld-Jakob's syndrome, bovine spongiform encephalopathy (BSE) or other prion related infections, diseases involving mitochondrial dysfunction, diseases involving β-amyloid and/or tauopathy such as Down's syndrome, hepatic encephalopathy, Huntington's disease, motor neuron diseases such as amyotrophic lateral sclerosis (ALS), multiple sclerosis (MS), olivoponto-cerebellar atrophy, post-operative cognitive deficit (POCD), Parkinson's disease, Parkinson's dementia, mild cognitive impairment, dementia pugilisitca, vascular and frontal lobe dementia, cognitive impairment, eye injuries or diseases (e.g. glaucoma, retinopathy, macular degeneration), head and spinal cord injuries/trauma, hypoglycaemia, hypoxia (e.g. perinatal), ischaemia (e.g. resulting from cardiac arrest, stroke, bypass operations or transplants), convulsions, glioma and other tumours, inner ear insult (e.g. in tinnitus, sound or drug-induced), L-dopa-induced and tardive dyskinesias, addiction (nicotine, alcohol, opiate, cocaine, amphetamine obesity and others), anxiety and panic disorders, attention deficit hyperactivity disorder (ADHD), restless leg syndrome, hyperactive children, autism, convulsions/epilepsy, dementia (e.g. in Alzheimer's disease, Korsakoff syndrome, vascular dementia, HIV infections), major depressive disorder or depression (including that resulting from Borna virus infection) and bipolar manic-depressive disorder, drug tolerance e.g. to opioids, movement disorders, dystonia, dyskinesia (e.g. L-Dopa-induced, tardive dyskinesia or in Huntington's disease), fragile-X syndrome, Huntington's chorea, irritable bowel syndrome (IBS), migraine, multiple sclerosis, muscle spasms, pain (chronic and acute, e.g. inflammatory pain, neuropathic pain, allodynia, hyperalgesia, nociceptive pain), Parkinson's disease, post traumatic stress disorder, schizophrenia (positive and negative symptoms), spasticity, Tourette's syndrome, urinary incontinence and vomiting, pruritic conditions (e.g. pruritus), sleep disorders, micturition disorders, neuromuscular disorder in the lower urinary tract, gastroesophageal reflux disease (GERD), lower esophageal sphincter (LES) disease, functional gastrointestinal disorders, dyspepsia, regurgitation, respiratory tract infection, bulimia nervosa, chronic laryngitis, asthma (e.g. reflux-related asthma), lung disease, eating disorders, obesity and obesity-related disorders, agoraphobia, generalized anxiety disorder, obsessive-compulsive disorder, panic disorder, posttraumatic stress disorder, social phobia, substance-induced anxiety disorder, delusional disorder, schizoaffective disorder, schizophreniform disorder, substance-induced psychotic disorder, delirium, or for cognitive enhancement or neuroprotection.

Such a medicament wherein the medicament is for the prevention and/or treatment of addiction, neuropathic pain, L-dopa-induced and tardive dyskinesias, ALS, fragile-X syndrome, Parkinson's disease, anxiety disorders, epilepsy, positive and/or negative symptoms of schizophrenia, cognitive impairment, or for cognitive enhancement and neuroprotection.

Further, a pharmaceutical composition comprising, together with one or more pharmaceutically acceptable excipients or vehicles, a compound of Formula I

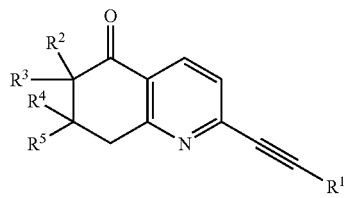

I wherein
  $R^1$ represents aryl or heteroaryl;
  $R^2$ and. $R^3$, which may be the same or different, represent hydrogen or $C_{1-6}$alkyl;
  $R^4$ and $R^5$, which may be the same or different, represent hydrogen or $C_{1-6}$alkyl;
  it being understood that:
  aryl represents an unsubstituted phenyl ring or a phenyl ring that is substituted with 1, 2, 3, 4 or 5 substituents, that may be the same or different, which substituents are selected from $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$ alkyl, hydroxyl, F, Cl, Br, I, CN, nitro, di-$C_{1-6}$alkylamino, N-cyclo$C_{3-12}$alkyl-N-$C_{1-6}$alkylamino, azetidinyl, pyrrolidinyl, piperidinyl, morpholinyl, 4-$C_{1-6}$-alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
  heteroaryl represents a (hetero)aromatic 5-, 6- or 7-membered ring having from 1 to 4 heteroatoms, said heteroatoms being independently selected from oxygen, nitrogen and sulfur, wherein said ring is unsubstituted or substituted with 1, 2 or 3 substituents, that may be the same or different, which substituents are selected from the group consisting of $C_{1-6}$-alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$ alkylamino, N-cyclo$C_{3-12}$alkyl-N-$C_{1-6}$alkylamino, azetidinyl, pyrrolidinyl, piperidinyl, morpholinyl, 4-$C_{1-6}$ alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;

and optical isomers, pharmaceutically acceptable salts, hydrates, solvates, and polymorphs thereof.

Specific compounds of Formula I within the present invention include but are not limited to:
2-Phenylethynyl-7,8-dihydro-6H-quinolin-5-one
2-Pyridin-3-ylethynyl-7,8-dihydro-6H-quinolin-5-one
2-m-Tolylethynyl-7,8-dihydro-6H-quinolin-5-one
2-(3-Hydroxy-phenylethynyl)-7,8-dihydro-6H-quinolin-5-one
2-(3-Methoxy-phenylethynyl)-7,8-dihydro-6H-quinolin-5-one
2-(3-Fluoro-phenylethynyl)-7,8-dihydro-6H-quinolin-5-one
2-(3-Chloro-phenylethynyl)-7,8-dihydro-6H-quinolin-5-one
2-(3-Bromo-phenylethynyl)-7,8-dihydro-6H-quinolin-5-one
3-(5-Oxo-5,6,7,8-tetrahydro-quinolin-2-ylethynyl)-benzonitrile
2-Thiazol-5-ylethynyl-7,8-dihydro-6H-quinolin-5-one
2-Oxazol-5-ylethynyl-7,8-dihydro-6H-quinolin-5-one
7,7-Dimethyl-2-pyridin-3-ylethynyl-7,8-dihydro-6H-quinolin-5-one
7,7-Dimethyl-2-m-tolylethynyl-7,8-dihydro-6H-quinolin-5-one
2-(3-Hydroxy-phenylethynyl)-7,7-dimethyl-7,8-dihydro-6H-quinolin-5-one
2-(3-Methoxy-phenylethynyl)-7,7-dimethyl-7,8-dihydro-6H-quinolin-5-one
2-(3-Fluoro-phenylethynyl)-7,7-dimethyl-7,8-dihydro-6H-quinolin-5-one
2-(3-Chloro-phenylethynyl)-7,7-dimethyl-7,8-dihydro-6H-quinolin-5-one
2-(3-Bromo-phenylethynyl)-7,7-dimethyl-7,8-dihydro-6H-quinolin-5-one
3-(7,7-Dimethyl-5-oxo-5,6,7,8-tetrahydro-quinolin-2-ylethynyl)-benzonitrile
7,7-Dimethyl-2-thiazol-5-ylethynyl-7,8-dihydro-6H-quinolin-5-one
7,7-Dimethyl-2-oxazol-5-ylethynyl-7,8-dihydro-6H-quinolin-5-one
2-(2-Phenyl-oxazol-5-ylethynyl)-7,8-dihydro-6H-quinolin-5-one
2-(2-Phenyl-thiazol-5-ylethynyl)-7,8-dihydro-6H-quinolin-5-one
2-Pyridin-2-ylethynyl-7,8-dihydro-6H-quinolin-5-one
7,7-Dimethyl-2-pyridin-2-ylethynyl-7,8-dihydro-6H-quinolin-5-one
6,6-Dimethyl-2-pyridin-3-ylethynyl-7,8-dihydro-6H-quinolin-5-one
2-(3-Fluoro-phenylethynyl)-6,6-dimethyl-7,8-dihydro-6H-quinolin-5-one
2-(3-Chloro-phenylethynyl)-6,6-dimethyl-7,8-dihydro-6H-quinolin-5-one
2-(3-Methoxy-phenylethynyl)-6,6-dimethyl-7,8-dihydro-6H-quinolin-5-one
2-(3-Hydroxy-phenylethynyl)-6,6-dimethyl-7,8-dihydro-6H-quinolin-5-one 3-(6,6-Dimethyl-5-oxo-5,6,7,8-tetrahydro-quinolin-2-yl-ethynyl)-benzonitrile
6,6-Dimethyl-2-thiazol-5-ylethynyl-7,8-dihydro-6H-quinolin-5-one
6,6-Dimethyl-2-(3-piperidin-1-yl-phenylethynyl)-7,8-dihydro-6H-quinolin-5-one
7,7-Dimethyl-2-(3-piperidin-1-yl-phenylethynyl)-7,8-dihydro-6H-quinolin-5-one
2-(3-Piperidin-1-yl-phenylethynyl)-7,8-dihydro-6H-quinolin-5-one
2-(3-Morpholin-4-yl-phenylethynyl)-7,8-dihydro-6H-quinolin-5-one
7,7-Dimethyl-2-(3-morpholin-4-yl-phenylethynyl)-7,8-dihydro-6H-quinolin-5-one
6,6-Dimethyl-2-(3-morpholin-4-yl-phenylethynyl)-7,8-dihydro-6H-quinolin-5-one
6,6-Dimethyl-2-[3-(1H-tetrazol-5-yl)-phenylethynyl]-7,8-dihydro-6H-quinolin-5-one
7,7-Dimethyl-2-[3-(1H-tetrazol-5-yl)-phenylethynyl]-7,8-dihydro-6H-quinolin-5-one
2-[3-(1H-Tetrazol-5-yl)-phenylethynyl]-7,8-dihydro-6H-quinolin-5-one
2-[3-Fluoro-5-(1H-tetrazol-5-yl)-phenylethynyl]-6,6-dimethyl-7,8-dihydro-6H-quinolin-5-one
2-[3-Fluoro-5-(1H-tetrazol-5-yl)-phenylethynyl]-7,7-dimethyl-7,8-dihydro-6H-quinolin-5-one
2-[3-Fluoro-5-(1H-tetrazol-5-yl)-phenylethynyl]-7,8-dihydro-6H-quinolin-5-one
2-(3-Trifluoromethyl-phenylethynyl)-7,8-dihydro-6H-quinolin-5-one
7,7-Dimethyl-2-(3-trifluoromethyl-phenylethynyl)-7,8-dihydro-6H-quinolin-5-one
6,6-Dimethyl-2-(3-trifluoromethyl-phenylethynyl)-7,8-dihydro-6H-quinolin-5-one
7,7-Dimethyl-2-phenylethynyl-7,8-dihydro-6H-quinolin-5-one
6,6-Dimethyl-2-phenylethynyl-7,8-dihydro-6H-quinolin-5-one
2-(4-Methyl-thiazol-2-ylethynyl)-7,8-dihydro-6H-quinolin-5-one
7,7-Dimethyl-2-(4-methyl-thiazol-2-ylethynyl)-7,8-dihydro-6H-quinolin-5-one
6,6-Dimethyl-2-(4-methyl-thiazol-2- ylethynyl)-7,8-dihydro-6H-quinolin-5-one
2-(4-Fluoro-thiazol-2-ylethynyl)-7,8-dihydro-6H-quinolin-5-one
2-(4-Fluoro-thiazol-2-ylethynyl)-7,7-dimethyl-7,8-dihydro-6H-quinolin-5-one
2-(4-Fluoro-thiazol-2-ylethynyl)-6,6-dimethyl-7,8-dihydro-6H-quinolin-5-one
2-(2-Phenyl-oxazol-5-ylethynyl)-7,8-dihydro-6H-quinolin-5-one
2-(2-Phenyl-thiazol-5-ylethynyl)-7,8-dihydro-6H-quinolin-5-one
2-(5-Fluoro-pyridin-3-ylethynyl)-7,8-dihydro-6H-quinolin-5-one
3-Fluoro-5-(7,7-Dimethyl-5-oxo-5,6,7,8-tetrahydro-quinolin-2-ylethynyl)-benzonitrile
2-(4-Fluoro-5-phenyl-oxazol-2-ylethynyl)-7,8-dihydro-6H-quinolin-5-one
2-(4-Fluoro-5-pyridin-3-yl-oxazol-2-ylethynyl)-7,8-dihydro-6H-quinolin-5-one
2-(4-Fluoro-5-pyridin-3-yl-oxazol-2-ylethynyl)-7,7-dimethyl-7,8-dihydro-6H-quinolin-5-one
2-(4-Fluoro-5-pyridin-3-yl-oxazol-2-ylethynyl)-6,6-dimethyl-7,8-dihydro-6H-quinolin-5-one
6,6-Dimethyl-2-pyridin-2-ylethynyl-7,8-dihydro-6H-quinolin-5-one
6,6-Dimethyl-2-(4-methyl-oxazol-2-ylethynyl)-7,8-dihydro-6H-quinolin-5-one
7,7-Dimethyl-2-(4-methyl-oxazol-2-ylethynyl)-7,8-dihydro-6H-quinolin-5-one
2-(4-Fluoro-5-pyridin-3-yl-1H-imidazol-2-ylethynyl)-7,8-dihydro-6H-quinolin-5-one
2-(4-Fluoro-5-pyridin-3-yl-1H-imidazol-2-ylethynyl)-7,7-dimethyl-7,8-dihydro-6H-quinolin-5-one
2-(4-Fluoro-5-pyridin-3-yl-1H-imidazol-2-ylethynyl)-6,6-dimethyl-7,8-dihydro-6H-quinolin-5-one
6,6-Dimethyl-2-(4-pyridin-3-yl-imidazol-1-ylethynyl)-7,8-dihydro-6H-quinolin-5-one
7,7-Dimethyl-2-(4-pyridin-3-yl-imidazol-1-ylethynyl)-7,8-dihydro-6H-quinolin-5-one
2-(4-Pyridin-3-yl-imidazol-1-ylethynyl)-7,8-dihydro-6H-quinolin-5-one
2-Thiazol-2-ylethynyl-7,8-dihydro-6H-quinolin-5-one
2-[1,3,4]Thiadiazol-2-ylethynyl-7,8-dihydro-6H-quinolin-5-one
2-[1,3,4]Oxadiazol-2-ylethynyl-7,8-dihydro-6H-quinolin-5-one
2-(1H-Tetrazol-5-ylethynyl)-7,8-dihydro-6H-quinolin-5-one
6,6-Dimethyl-2-[1,3,4]thiadiazol-2-ylethynyl-7,8-dihydro-6H-quinolin-5-one
7,7-Dimethyl-2-[1,3,4]thiadiazol-2-ylethynyl-7,8-dihydro-6H-quinolin-5-one
7,7-Dimethyl-2-(1H-tetrazol-5-ylethynyl)-7,8-dihydro-6H-quinolin-5-one
6,6-Dimethyl-2-(1H-tetrazol-5-ylethynyl)-7,8-dihydro-6H-quinolin-5-one
6,6-Dimethyl-2-oxazol-5-ylethynyl-7,8-dihydro-6H-quinolin-5-one
2-Oxazol-2-ylethynyl-7,8-dihydro-6H-quinolin-5-one
6,6-Dimethyl-2-oxazol-2-ylethynyl-7,8-dihydro-6H-quinolin-5-one
7,7-Dimethyl-2-oxazol-2-ylethynyl-7,8-dihydro-6H-quinolin-5-one
6,6-Dimethyl-2-m-tolylethynyl-7,8-dihydro-6H-quinolin-5-one
7,7-Dimethyl-2-(2-phenyl-oxazol-5-ylethynyl)-7,8-dihydro-6H-quinolin-5-one
6,6-Dimethyl-2-(2-phenyl-oxazol-5-ylethynyl)-7,8-dihydro-6H-quinolin-5-one
7,7-Dimethyl-2-(5-phenyl-thiazol-2-ylethynyl)-7,8-dihydro-6H-quinolin-5-one
6,6-Dimethyl-2-(5-phenyl-thiazol-2-ylethynyl)-7,8-dihydro-6H-quinolin-5-one
2-(5-Fluoro-pyridin-3-ylethynyl)-7,7-dimethyl-7,8-dihydro-6H-quinolin-5-one
2-(5-Fluoro-pyridin-3-ylethynyl)-6,6-dimethyl-7,8-dihydro-6H-quinolin-5-one
3-Fluoro-5-(5-oxo-5,6,7,8-tetrahydro-quinolin-2-ylethynyl)-benzonitrile
3-(6,6-Dimethyl-5-oxo-5,6,7,8-tetrahydro-quinolin-2-yl-ethynyl)-5-fluoro-benzonitrile
2-(4-Fluoro-5-phenyl-oxazol-2-ylethynyl)-7,7-dimethyl-7,8-dihydro-6H-quinolin-5-one
2-(4-Fluoro-5-phenyl-oxazol-2-ylethynyl)-6,6-dimethyl-7,8-dihydro-6H-quinolin-5-one
6,6-Dimethyl-2-(5-pyridin-3-yl-[1,3,4]oxadiazol-2-ylethynyl)-7,8-dihydro-6H-quinolin-5-one
7,7-Dimethyl-2-(5-pyridin-3-yl-[1,3,4]oxadiazol-2-ylethynyl)-7,8-dihydro-6H-quinolin-5-one 2-(5-Pyridin-3-yl-[1,3,4]oxadiazol-2-ylethynyl)-7,8-dihydro-6H-quinolin-5-one and optical isomers, pharmaceutically acceptable salts, hydrates, solvates, and polymorphs thereof.

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms, inclusive, (i.e., methyl, ethyl, propyl, and isopropyl), straight and branched forms thereof.

As used herein, the term "$C_{1-6}$alkyl" comprises straight or branched chain alkyl groups having 1, 2, 3, 4, 5 or 6 carbon atoms. Said alkyl groups may be unsubstituted and include, e.g., methyl, ethyl, n-propyl, 2-propyl, n-butyl, tert-butyl. Further, these alkyl groups may optionally be substituted by one or more fluorine, chlorine and/or bromine atoms; examples of these halogenated alkyl moieties include —$CH_3$, —$C_2F_5$, —$CBr_3$, and —$CCl_3$. The term "$C_{1-6}$alkoxy" comprises straight or branched chain —O—$C_{1-6}$alkyl groups wherein "$C_{1-6}$alkyl" is defined as given hereinbefore. Examples of "$C_{1-6}$-alkoxy" include methoxy, ethoxy, n-propoxy, i-propoxy. A $C_{1-6}$alkoxy group optionally may be substituted by one or more fluorine, chlorine and/or bromine atoms thereby forming, for instance, —$OCF_3$, —$OC_2F_5$, —$CBr_3$. The term "cyclo$C_{3-12}$alkyl" represents monocyclic, bicyclic or tricyclic alkyl groups having 3, 4, 5, 6, 7, 8, 9, 10, 11 or 12 carbon atoms and includes cyclopropyl, cyclobutyl, cyclopentyl, cyclohexyl, bicyclo[2.2.1]heptyl and adamantyl. A cyclo$C_{3-12}$alkyl group optionally may be substituted with one or more fluorine, chlorine and/or bromine atoms. In the context of the present invention the term "di-$C_{1-6}$alkylamino" refers to an amino moiety in which the nitrogen atom of the amino group is substituted with two $C_{1-6}$alkyl groups, that may be the same or different, as defined above. Examples of di-$C_{1-6}$alkylamino groups include dimethylamino, diethylamino and N-methyl-N-isopropylamino. The term "N-cyclo$C_{3-2}$alkyl-N-$C_{1-6}$alkylamino" comprises amino groups in which the nitrogen atom of the amino group is substituted by one $C_{1-6}$alkyl group and one N-cyclo$C_{3-12}$alkyl group. Both the $C_{1-6}$alkyl group and the N-cyclo$C_{3-12}$alkyl group are defined as given hereinbefore. The term "4-$C_{1-6}$alkyl-piperazinyl" comprises piperazinyl radicals bearing a $C_{1-6}$alkyl moiety at the nitrogen atom in 4-position of the piperazine ring, said "$C_{1-6}$alkyl" having the same meaning as given hereinbefore. The term "(hetero)aromatic 5-, 6- or 7-membered ring" refers to heterocyclic rings having up to 4 oxygen, nitrogen and/or sulfur atoms in the ring that comprises 5, 6 or 7 carbon and hetero atoms, said heterocyclic ring being an aromatic ring system. Examples of such (hetero)aromatic 5-, 6- or 7-membered rings include unsubstituted or appropriately substituted pyrroles, oxazoles, thiophenes, furans, isoxazoles, imidazoles, oxazoles, oxadiazoles, thiazoles, imidazolines, pyrazoles, oxazolidines, isooxazolidines, thiazolidines, pyridines, pyridazines, pyrimidines, pyrazines, azepines. The term "halogen" represents fluorine, chlorine, bromine and iodine.

The compounds of the present invention are named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, and "rt" for room temperature).

The term "analog" or "derivative" is used herein in the conventional pharmaceutical sense, to refer to a molecule that structurally resembles a reference molecule (such as 7,8-dihydro-6H-quinolin-5-one), but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

In addition, using methods known to those skilled in the art, analogs and derivatives of the compounds of the invention can be created which have improved therapeutic efficacy in controlling dementia, i.e., higher potency and/or selectivity at a specific targeted receptor type, either greater or lower ability to penetrate mammalian blood-brain barriers (e.g., either higher or lower blood-brain barrier permeation rate), fewer side effects, etc.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Compounds of the present invention may be in the form of pharmaceutically acceptable salts. "Pharmaceutically acceptable salts" refers to those salts which possess the biological effectiveness and properties of the parent compound and which are not biologically or otherwise undesirable. The nature of the salt or isomer is not critical, provided that it is non-toxic and does not substantially interfere with the desired pharmacological activity.

It will be appreciated by those skilled in the art that compounds of the invention having a chiral center may exist in and be isolated in optically active and racemic forms. Some compounds may exhibit polymorphism. It is to be understood that the present invention ecompasses any racemic, optically-active, polymorphic, tautomeric, or stereoisomeric form, or mixture thereof, of a compound of the invention, which possesses the useful properties described herein.

The following Scheme 1 describes the preparation of compounds of Formula I of the present invention. All of the starting materials are prepared by procedures described in the scheme, by procedures well known to one of ordinary skill in organic chemistry or can be obtained commercially. All of the final compounds of the present invention are prepared by procedures described in this chart or by procedures analogous thereto, which would be well known to one of ordinary skill in organic chemistry. All of the variables used in the scheme are as defined below or as in the claims.

A synthetic procedure toward 2-substituted-ethynyl-7,8-dihydro-6H-quinolin-5-ones with the general Formula I is given in Scheme 1. The reaction of appropriately functionalized cyclohexane-1,3-dione derivatives 1 with ammonium acetate/acetic acid in benzene yields the corresponding 3-amino-cyclohex-2-enone derivatives 2. Compound 2 is then reacted with alkyl propiolate and cyclization is achieved at elevated temperatures to form the quinoline-2,5-dione 3. Subsequent reaction with phosphoryl chloride gives the 2-chloro-substituted quinolin-5-one derivative 4. Substitution of the chloro-substituent with an appropriate acetylene derivative under palladium (0) catalysis in the presence of base yields compounds of Formula I.

Scheme 1 Synthesis of 2-substituted-ethynyl-7,8-dihydro-6H-quinolin-5-ones

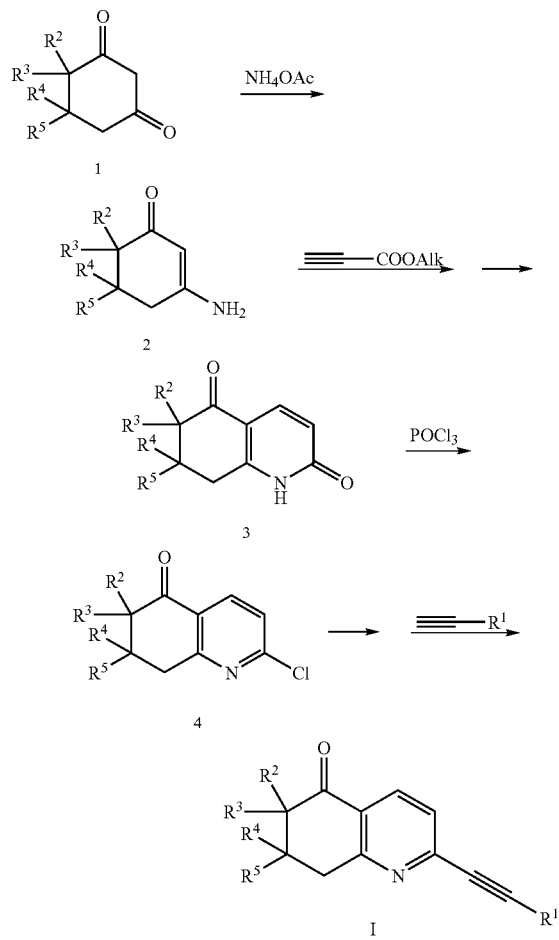

It will be apparent to those skilled in the art that the described synthetic procedures are merely representative in nature and that alternative synthetic processes are known to one of ordinary skill in organic chemistry.

EXPERIMENTAL PART

The compounds and their preparation of the present invention will be better understood in connection with the following examples, which are intended as an illustration of and not a limitation upon the scope of the invention.

Hereinafter, "DMF" is defined as N,N-dimethylformamide, "HCl" as hydrochloric acid, "DMSO" as dimethylsulfoxide and "TMS" as tetramethylsilane.

Preparation 1

3-Amino-5,5-dimethylcyclohex-2-en-1-one

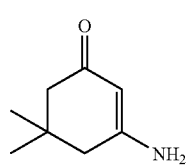

The title compound was prepared according to (Baraldi, P. G.; Simoni, D.; Manfredini, S.; *Synthesis* 1983, (11) 902-903.) as a colorless solid in 76% yield.

Preparation 2

7,7-Dimethyl-7,8-dihydro-1H,6H-quinoline-2,5-dione

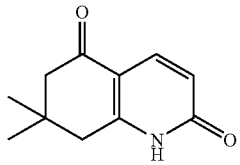

In analogy to (Pettit, G. R.; Fleming, W. C.; Paull, K. D. *J. Org. Chem.* 1968, 33 (3) 1089-1092.), 3-amino-5,5-dimethylcyclohex-2-en-1-one was reacted with ethyl propio-late to give the title compound as a light brown solid in 78.5% yield.

Physical characteristics are as follows:
$^1$H NMR (CDCl$_3$, TMS) δ: 1.14, 2.42, 2.82, 6.47, and 8.04.

Preparation 3

2-Chloro-7,7-dimethyl-7,8-dihydro-6H-quinolin-5-one

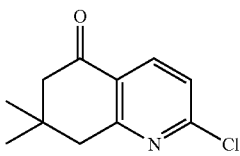

In analogy to (Shanazarov, A. K.; Kuzovkin, V. A.; Chistjakov, V. V.; Granik, V. G. *Khim. Geterotsikl. Soedin.* 1991, (1) 86-92.) 7,7-dimethyl-7,8-dihydro-1H,6H-quinoline-2,5-dione was treated with phosphoryl chloride (POCl$_3$) to give the title compound as a gray solid in 60% yield.

Physical characteristics are as follows:
$^1$H NMR (CDCl$_3$, TMS) δ:1.11, 2.54, 3.01, 7.30, and 8.30.

Preparation 4

3-Amino-5-ethylcyclohex-2-en-1-one

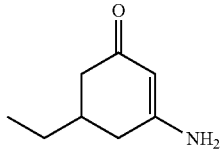

In close analogy to (Baraldi, P. G.; Simoni, D.; Manfredini, S.; *Synthesis* 1983, (11) 902-903) 5-ethylcyclohexane-1,3-dione was reacted with ammonium acetate to give the title compound.

Physical characteristics are as follows:
$^1$H NMR (CDCl$_3$, TMS) δ: 0.93 (t, 6.5 Hz, 3H); 1.42 (m, 2H); 1.88-2.44 (m, 5H); 4.62 (br s, 2H) and 5.23 ppm (s, 1H).

Preparation 5

3-Amino-6-propylcyclohex-2-en-1-one

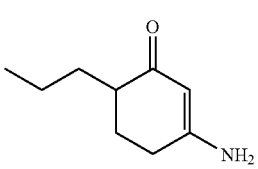

In close analogy to (Baraldi, P. G.; Simoni, D.; Manfredini, S.; Synthesis 1983, (11) 902-903) 4-propylcyclohexane-1,3-dione was reacted with ammonium acetate to give the title compound as a colorless solid.

Physical characteristics are as follows:
¹H NMR (CDCl3, TMS) δ: 0.91 (t, 7Hz, 3H); 1.25-1.90 (m, 5H); 1.98-2.18 (m, 2H); 2.35 (t, 6Hz, 2H); 4.50 (br s, 2H) and 5.19 ppm (s, 1H).

Preparation 6

3-Amino-5-isopropylcyclohex-2-en-1-one

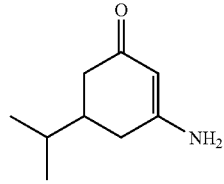

In analogy to (Baraldi, P. G.; Simoni, D.; Manfredini, S.; *Synthesis* 1983, (11) 902-903) 5-isopropylcyclohexane-1,3-dione was reacted with ammonium acetate to give the title compound as a colorless solid.

Physical characteristics are as follows:
¹H NMR (CDCl3, TMS) δ: 0.91 (d, 6.5Hz); 1.48-1.65 (m, 1H); 1.84-2.39 (m, 5H); 5.04 (br s, 2H) and 5.22 ppm (s, 1H).

Preparation 7

3-Amino-6,6-dimethylcyclohex-2-en-1-one

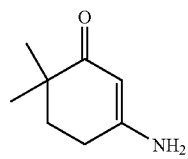

In analogy to (Baraldi, P. G.; Simoni, D.; Manfredini, S.; Synthesis 1983, (11) 902-903) 4,4-dimethylcyclohexane-1,3-dione was reacted with ammonium acetate to give the title compound as a colorless solid.

Physical characteristics are as follows:
Mp 153-154-° C.; 1H NMR (DMSO-D6, TMS) δ: 0.94 (s, 6H); 1.64 (t, 6.5Hz, 2H); 2.28 (t, 6.5Hz, 2H); 4.79 (s, 1H) and 6.58 ppm (br s, 2H).

Preparation 8

3-Amino-6-ethyl-6-methylcyclohex-2-en-1-one

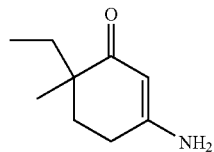

In analogy to (Baraldi, P. G.; Simoni, D.; Manfredini, S.; Synthesis 1983, (11) 902-903) 4-ethyl-4-methylcyclohexane-1,3-dione was reacted with ammonium acetate to give the title compound as a colorless solid.

Physical characteristics are as follows:
-¹H NMR (CDCl3, TMS) δ: 0.83 (t, 6.5Hz, 3H); 1.06 (s, 3H); 1.40-1.80 (m, 3H); 1.85-2.00 (m, 1H); 2.35 (t, 6.5Hz, 2H); 4.31 (br s, 2H) and 5.14 ppm (s,1H). Mp 99-100° C.; ¹H NMR (CDCl₃, TMS) δ: 1.08, 1.73, 2.45, 2.79, 3.91, and 8.33; Anal. Found (C₁₇H₂₁N₃O) (%): C, 71.6;H, 7.5; N, 14.4

EXAMPLE 1

2-Phenylethynyl-7,8-dihydro-6H-quinolin-5-one

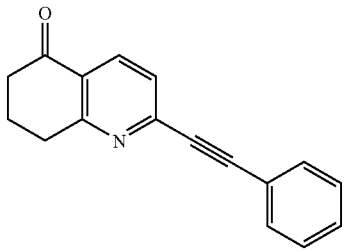

To a solution of 2-chloro-7,8-dihydro-6H-quinolin-5-one (0.2 g, 1.1 mmol) and ethynylbenzene (0.17 g, 1.6 mmol) in triethylamine (7 ml) under an argon atmosphere was added tetrakis (triphenylphosphine) palladium (0.02 g, 0.062 mmol). The mixture was heated at reflux for 3 h. Then it was concentrated under reduced pressure and the residue was purified by column chromatography on silica gel to give the title compound (0.04 g, 15%).

Physical characteristics are as follows:
Mp 121-122° C.; ¹H NMR (CDCl₃, TMS) δ: 2.20 (2H); 2.68 (2H); 3.17 (2H); 7.22-7.38 (3H); 7.46 (1H); 7.60 (2H); 8.24 (1H); MS 248 (M+1).

EXAMPLE 2

2-Pyridin-3-ylethynyl-7,8-dihydro-6H-quinolin-5-one

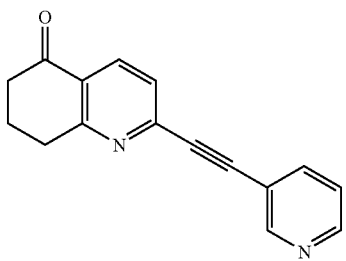

In analogy to the procedure described in Example 1, the title compound was obtained in moderate yield (120 mg, 15%, MP: 120-122.1° C.).

EXAMPLE 3

6,6-Dimethyl-2-phenylethynyl-7,8-dihydro-6H-quinolin-5-one

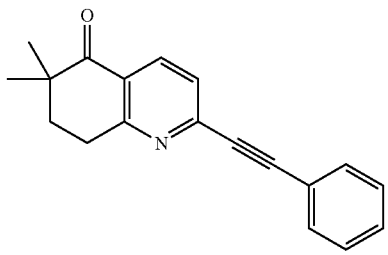

In analogy to the procedure described in Example 1, the title compound is obtained in moderate yield.

EXAMPLE 4

7,7-Dimethyl-2-pyridin-3-ylethynyl-7,8-dihydro-6H-quinolin-5-one

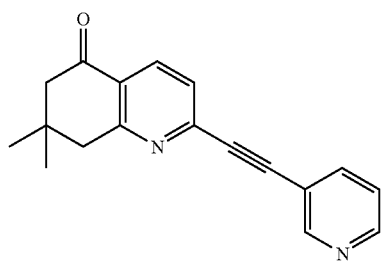

In analogy to the procedure described in Example 1, the title compound was obtained in moderate yield (50 mg, 12%, MP: 108-109.2° C.).

EXAMPLE 5

6,6-Dimethyl-2-pyridin-3-ylethynyl-7,8-dihydro-6H-quinolin-5-one

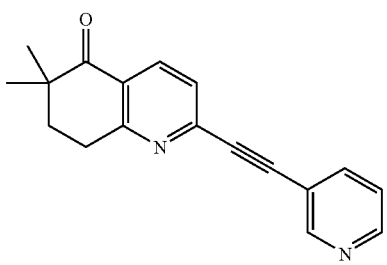

In analogy to the procedure described in Example 1, the title compound is obtained in moderate yield.

EXAMPLE 6

2-m-Tolylethynyl-7,8-dihydro-6H-quinolin-5-one

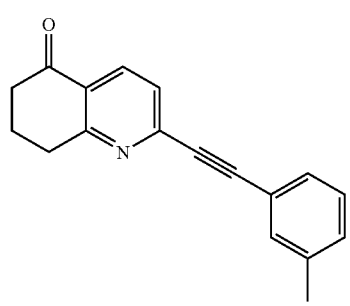

In analogy to the procedure described in Example 1, the title compound is obtained in moderate yield.

EXAMPLE 7

6,6-Dimethyl-2-m-tolylethynyl-7,8-dihydro-6H-quinolin-5-one

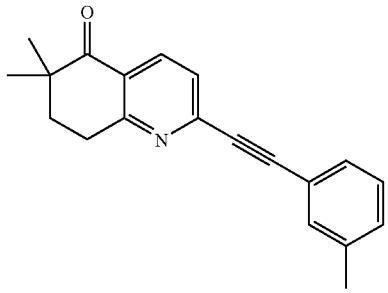

In analogy to the procedure described in Example 1, the title compound is obtained in moderate yield

EXAMPLE 8

2-(3-Hydroxy-phenylethynyl)-7,8-dihydro-6H-quinolin-5-one

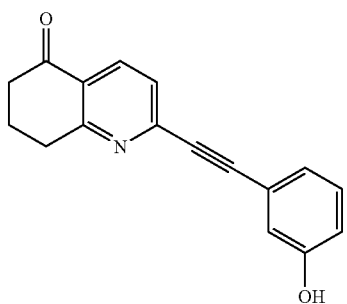

In analogy to the procedure described in Example 1, the title compound is obtained in moderate yield.

EXAMPLE 9

2-(3-Methoxy-phenylethynyl)-7,8-dihydro-6H-quinolin-5-one

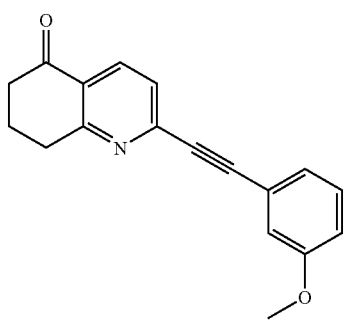

In analogy to the procedure described in Example 1, the title compound is obtained in moderate yield.

EXAMPLE 10

2-(3-Methoxy-phenylethynyl)-6,6-dimethyl-7,8-dihydro-6H-quinolin-5-one

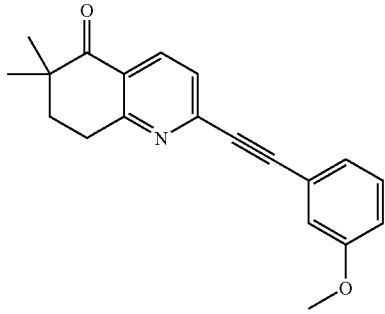

In analogy to the procedure described in Example 1, the title compound is obtained in moderate yield.

EXAMPLE 11

2-(3-Fluoro-phenylethynyl)-7,8-dihydro-6H-quinolin-5-one

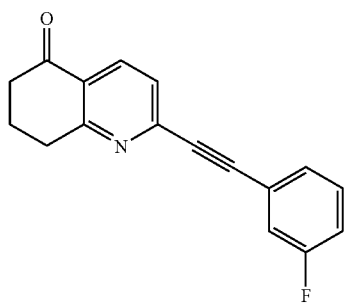

In analogy to the procedure described in Example 1, the title compound is obtained in moderate yield.

EXAMPLE 12

2-(3-Fluoro-phenylethynyl)-6,6-dimethyl-7,8-dihydro-6H-quinolin-5-one

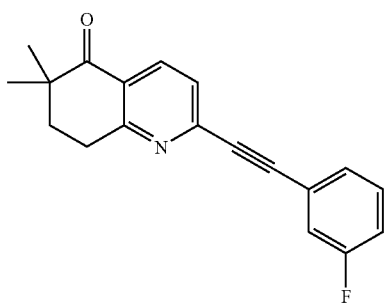

In analogy to the procedure described in Example 1, the title compound is obtained in moderate yield.

EXAMPLE 13

2-(3-Chloro-phenylethynyl)-7,8-dihydro-6H-quinolin-5-one

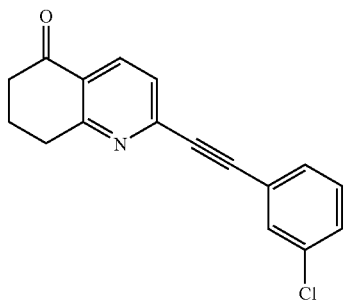

In analogy to the procedure described in Example 1, the title compound is obtained in moderate yield.

EXAMPLE 14

2-(3-Bromo-phenylethynyl)-7,8-dihydro-6H-quinolin-5-one

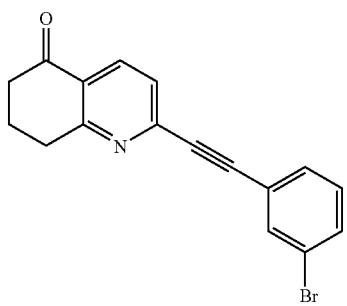

In analogy to the procedure described in Example 1, the title compound is obtained in moderate yield.

EXAMPLE 15

3-(5-Oxo-5,6,7,8-tetrahydro-quinolin-2-ylethynyl)-benzonitrile

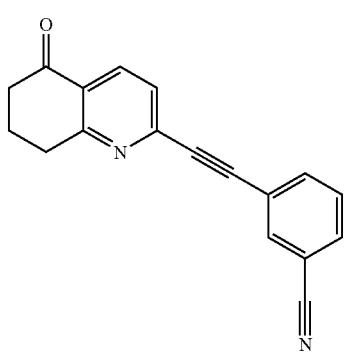

In analogy to the procedure described in Example 1, the title compound is obtained in moderate yield.

EXAMPLE 16

2-Thiazol-5-ylethynyl-7,8-dihydro-6H-quinolin-5-one

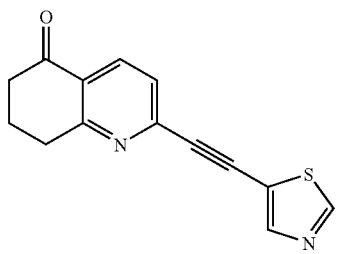

In analogy to the procedure described in Example 1, the title compound is obtained in moderate yield.

EXAMPLE 17

2-Thiazol-2-ylethynyl-7,8-dihydro-6H-quinolin-5-one

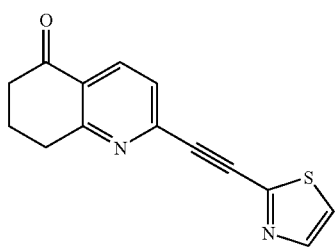

In analogy to the procedure described in Example 1, the title compound is obtained in moderate yield.

EXAMPLE 18

2-(4-Methyl-thiazol-2-ylethynyl)-7,8-dihydro-6H-quinolin-5-one

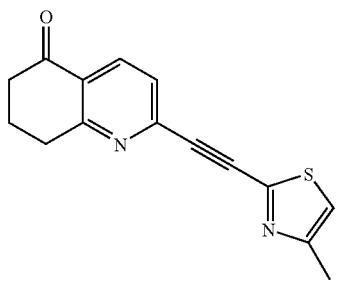

In analogy to the procedure described in Example 1, the title compound is obtained in moderate yield.

EXAMPLE 19

7,7-Dimethyl-2-(4-methyl-thiazol-2-ylethynyl)-7,8-dihydro-6H-quinolin-5-one

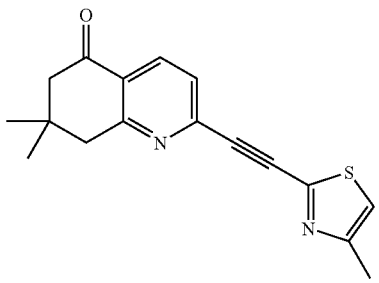

In analogy to the procedure described in Example 1, the title compound is obtained in moderate yield.

EXAMPLE 20

6,6-Dimethyl-2-(4-methyl-thiazol-2-ylethynyl)-7,8-dihydro-6H-quinolin-5-one

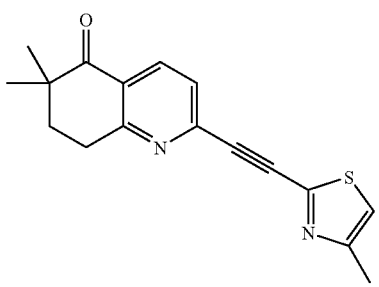

In analogy to the procedure described in Example 1, the title compound is obtained in moderate yield.

EXAMPLE 21

2-(4-Fluoro-thiazol-2-ylethynyl)-7,8-dihydro-6H-quinolin-5-one

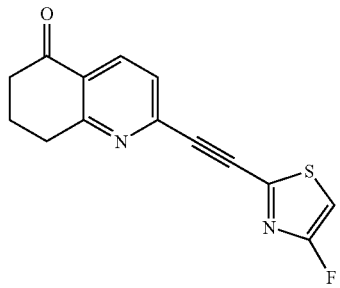

In analogy to the procedure described in Example 1, the title compound is obtained in moderate yield.

EXAMPLE 22

2-(4-Fluoro-thiazol-2-ylethynyl)-7,7-dimethyl-7,8-dihydro-6H-quinolin-5-one

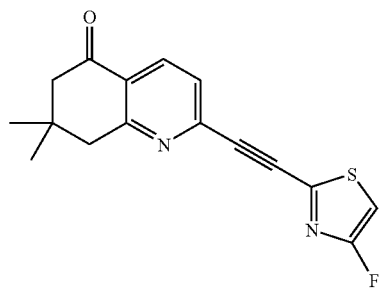

In analogy to the procedure described in Example 1, the title compound is obtained in moderate yield.

EXAMPLE 23

2-(4-Fluoro-thiazol-2-ylethynyl)-6,6-dimethyl-7,8-dihydro-6H-quinolin-5-one

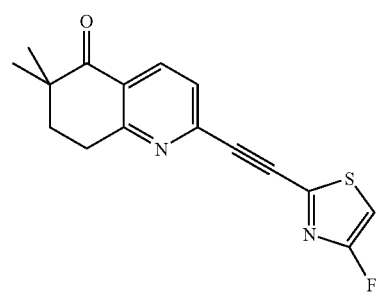

In analogy to the procedure described in Example 1, the title compound is obtained in moderate yield.

EXAMPLE 24

2-Oxazol-5-ylethynyl-7,8-dihydro-6H-quinolin-5-one

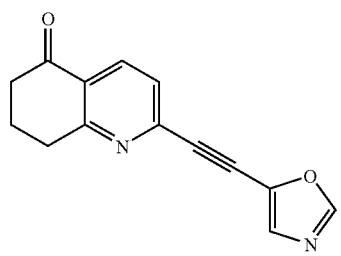

In analogy to the procedure described in Example 1, the title compound is obtained in moderate yield.

EXAMPLE 25

2-(2-Phenyl-oxazol-5-ylethynyl)-7,8-dihydro-6H-quinolin-5-one

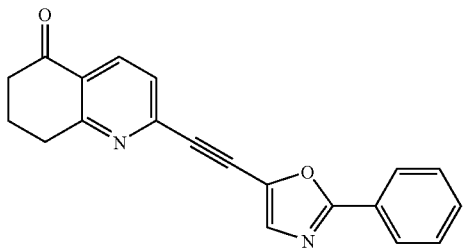

In analogy to the procedure described in Example 1, the title compound is obtained in moderate yield.

EXAMPLE 26

2-(2-Phenyl-thiazol-5-ylethynyl)-7,8-dihydro-6H-quinolin-5-one

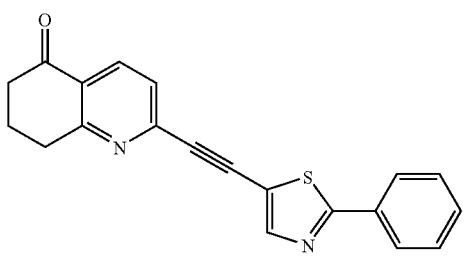

In analogy to the procedure described in Example 1, the title compound is obtained in moderate yield.

EXAMPLE 27

7,7-Dimethyl-2-m-tolylethynyl-7,8-dihydro-6H-quinolin-5-one

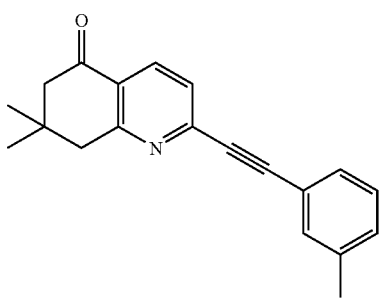

In analogy to the procedure described in Example 1, the title compound is obtained in moderate yield.

EXAMPLE 28

2-(3-Hydroxy-phenylethynyl)-7,7-dimethyl-7,8-dihydro-6H-quinolin-5-one

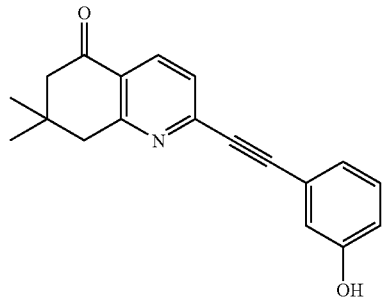

In analogy to the procedure described in Example 1, the title compound is obtained in moderate yield.

EXAMPLE 29

2-(3-Methoxy-phenylethynyl)-7,7-dimethyl-7,8-dihydro-6H-quinolin-5-one

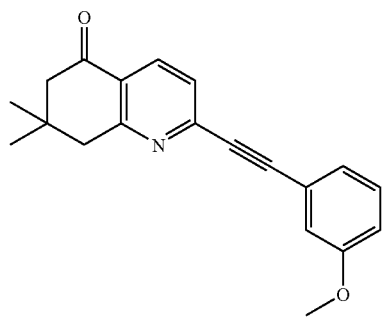

In analogy to the procedure described in Example 1, the title compound is obtained in moderate yield.

EXAMPLE 30

2-(3-Fluoro-phenylethynyl)-7,7-dimethyl-7,8-dihydro-6H-quinolin-5-one

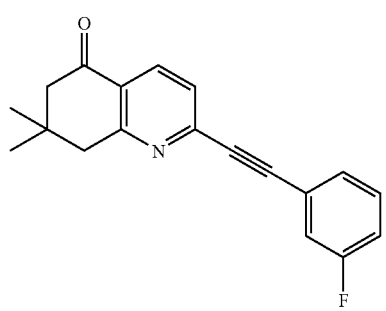

In analogy to the procedure described in Example 1, the title compound is obtained in moderate yield.

EXAMPLE 31

2-(3-Chloro-phenylethynyl)-7,7-dimethyl-7,8-dihydro-6H-quinolin-5-one

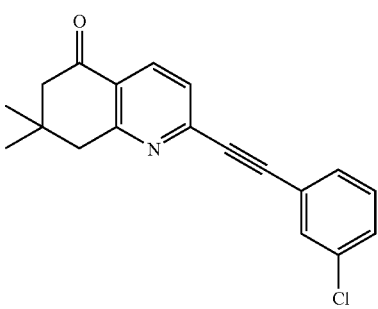

In analogy to the procedure described in Example 1, the title compound is obtained in moderate yield.

EXAMPLE 32

2-(3-Bromo-phenylethynyl)-7,7-dimethyl-7,8-dihydro-6H-quinolin-5-one

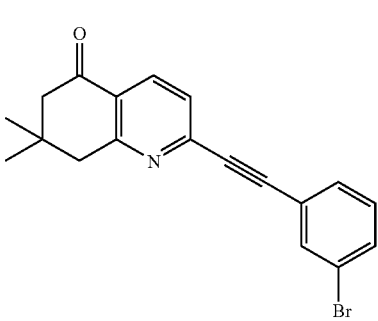

In analogy to the procedure described in Example 1, the title compound is obtained in moderate yield.

EXAMPLE 33

3-(7,7-Dimethyl-5-oxo-5,6,7,8-tetrahydro-quinolin-2-ylethynyl)-benzonitrile

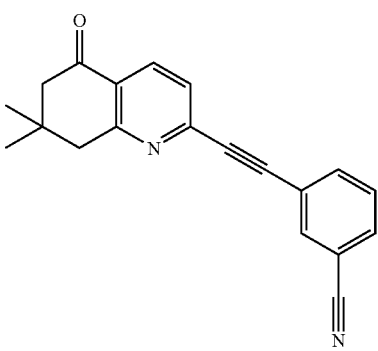

In analogy to the procedure described in Example 1, the title compound is obtained in moderate yield.

EXAMPLE 34

7,7-Dimethyl-2-thiazol-5-ylethynyl-7,8-dihydro-6H-quinolin-5-one

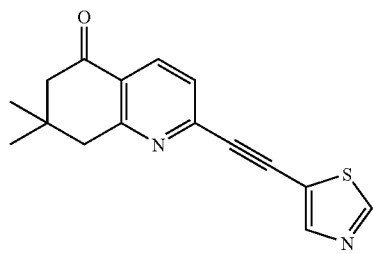

In analogy to the procedure described in Example 1, the title compound is obtained in moderate yield.

EXAMPLE 35

7,7-Dimethyl-2-oxazol-5-ylethynyl-7,8-dihydro-6H-quinolin-5-one

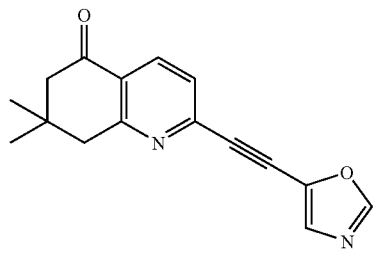

In analogy to the procedure described in Example 1, the title compound is obtained in moderate yield.

EXAMPLE 36

2-(5-Fluoro-pyridin-3-ylethynyl)-7,8-dihydro-6H-quinolin-5-one

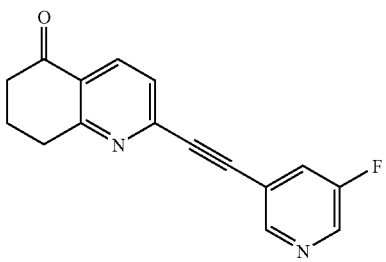

In analogy to the procedure described in Example 1, the title compound is obtained in moderate yield.

EXAMPLE 37

3-Fluoro-5-(7,7-Dimethyl-5-oxo-5,6,7,8-tetrahydro-quinolin-2-ylethynyl)-benzonitrile

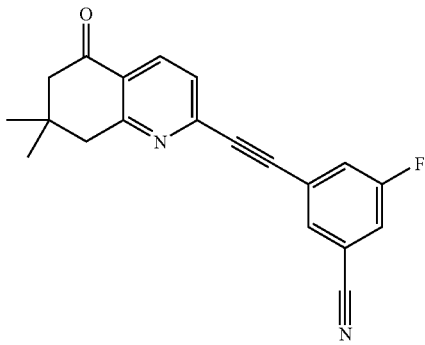

In analogy to the procedure described in Example 1, the title compound is obtained in moderate yield.

EXAMPLE 38

2-(4-Fluoro-5-phenyl-oxazol-2-ylethynyl)-7,8-dihydro-6H-quinolin-5-one

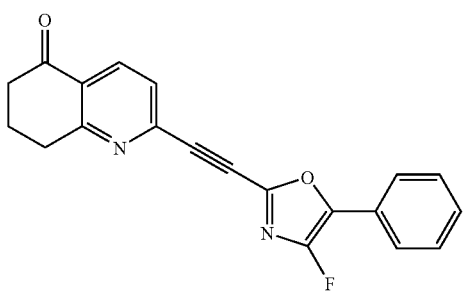

In analogy to the procedure described in Example 1, the title compound is obtained in moderate yield.

EXAMPLE 39

2-(4-Fluoro-5-pyridin-3-yl-oxazol-2-ylethynyl)-7,8-dihydro-6H-quinolin-5-one

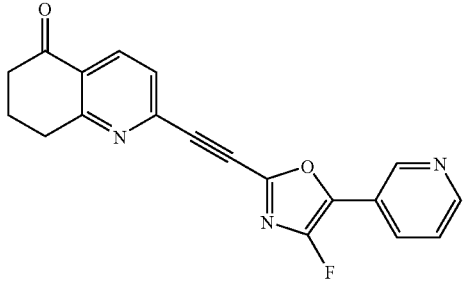

In analogy to the procedure described in Example 1, the title compound is obtained in moderate yield.

EXAMPLE 40

2-(4-Fluoro-5-pyridin-3-yl-oxazol-2-ylethynyl)-7,7-dimethyl-7,8-dihydro-6H-quinolin-5-one

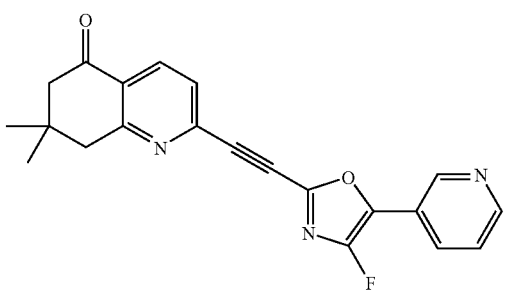

In analogy to the procedure described in Example 1, the title compound is obtained in moderate yield.

EXAMPLE 41

2-(4-Fluoro-5-pyridin-3-yl-oxazol-2-ylethynyl)-7,7-dimethyl-7,8-dihydro-6H-quinolin-5-one

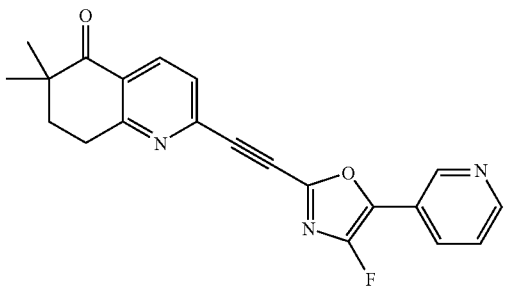

In analogy to the procedure described in Example 1, the title compound is obtained in moderate yield.

EXAMPLE 42

7,7-Dimethyl-2-pyridin-2-ylethynyl-7,8-dihydro-6H-quinolin-5-one

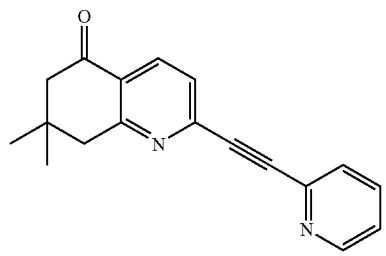

In analogy to the procedure described in Example 1, the title compound is obtained in moderate yield.

EXAMPLE 43

2-Pyridin-2-ylethynyl-7,8-dihydro-6H-quinolin-5-one

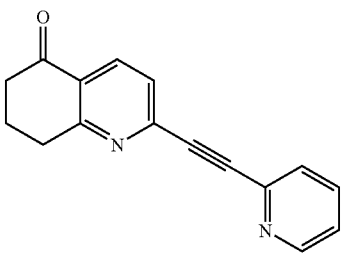

In analogy to the procedure described in Example 1, the title compound is obtained in moderate yield.

EXAMPLE 44

2-(3-Chloro-phenylethynyl)-6,6-dimethyl-7,8-dihydro-6H-quinolin-5-one

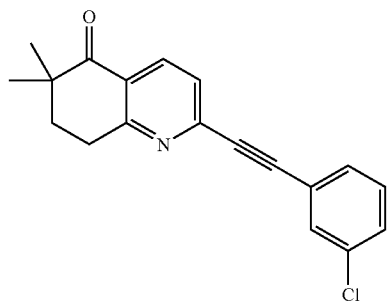

In analogy to the procedure described in Example 1, the title compound is obtained in moderate yield.

EXAMPLE 45

2-(3-Hydroxy-phenylethynyl)-6,6-dimethyl-7,8-dihydro-6H-quinolin-5-one

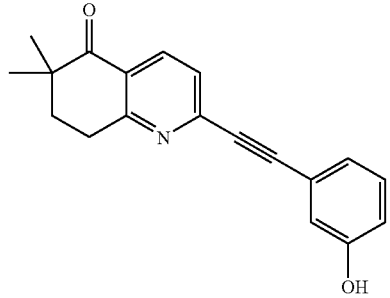

In analogy to the procedure described in Example 1, the title compound is obtained in moderate yield.

EXAMPLE 46

3-(6,6-Dimethyl-5-oxo-5,6,7,8-tetrahydro-quinolin-2-ylethynyl)-benzonitrile

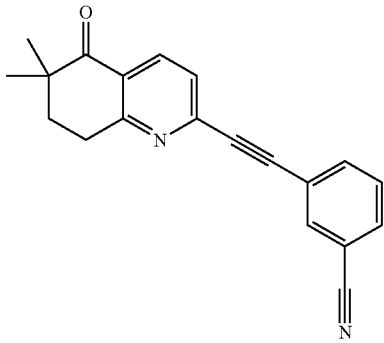

In analogy to the procedure described in Example 1, the title compound is obtained in moderate yield.

EXAMPLE 47

6,6-Dimethyl-2-thiazol-5-ylethynyl-7,8-dihydro-6H-quinolin-5-one

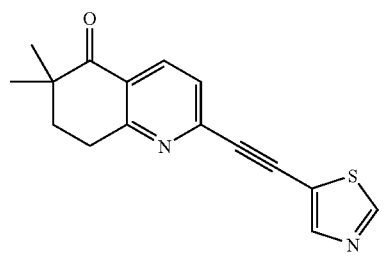

In analogy to the procedure described in Example 1, the title compound is obtained in moderate yield.

EXAMPLE 48

6,6-Dimethyl-2-(3-piperidin-1-yl-phenylethynyl)-7,8-dihydro-6H-quinolin-5-one

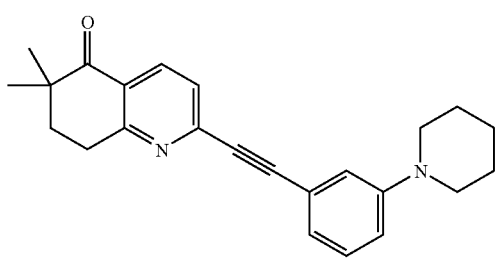

In analogy to the procedure described in Example 1, the title compound is obtained in moderate yield.

EXAMPLE 49

7,7-Dimethyl-2-(3-piperidin-1-yl-phenylethynyl)-7,8-dihydro-6H-quinolin-5-one

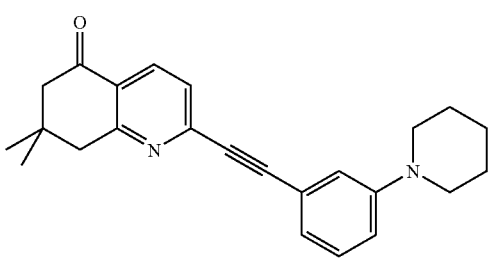

In analogy to the procedure described in Example 1, the title compound is obtained in moderate yield.

EXAMPLE 50

2-(3-Piperidin-1-yl-phenylethynyl)-7,8-dihydro-6H-quinolin-5-one

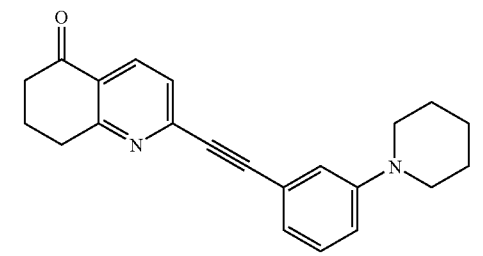

In analogy to the procedure described in Example 1, the title compound is obtained in moderate yield.

EXAMPLE 51

2-(3-Morpholin-4-yl-phenylethynyl)-7,8-dihydro-6H-quinolin-5-one

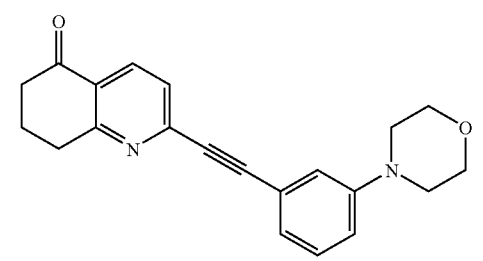

In analogy to the procedure described in Example 1, the title compound is obtained in moderate yield.

EXAMPLE 52

7,7-Dimethyl-2-(3-morpholin-4-yl-phenylethynyl)-7,8-dihydro-6H-quinolin-5-one

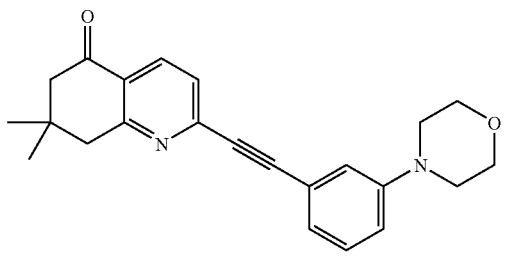

In analogy to the procedure described in Example 1, the title compound is obtained in moderate yield.

EXAMPLE 53

6,6-Dimethyl-2-(3-morpholin-4-yl-phenylethynyl)-7,8-dihydro-6H-quinolin-5-one

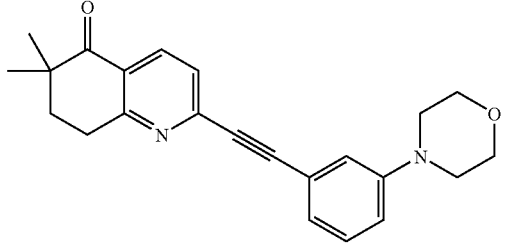

In analogy to the procedure described in Example 1, the title compound is obtained in moderate yield.

EXAMPLE 54

6,6-Dimethyl-2-[3-(1H-tetrazol-5-yl)-phenylethynyl]-7,8-dihydro-6H-quinolin-5-one

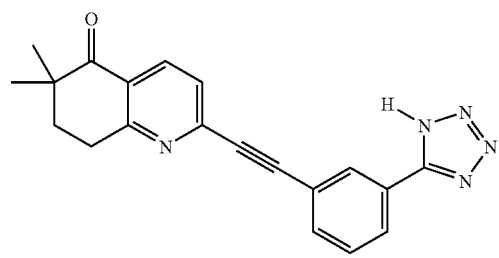

In analogy to the procedure described in Example 1, the title compound is obtained in moderate yield.

EXAMPLE 55

7,7-Dimethyl-2-[3-(1H-tetrazol-5-yl)-phenylethynyl]-7,8-dihydro-6H-quinolin-5-one

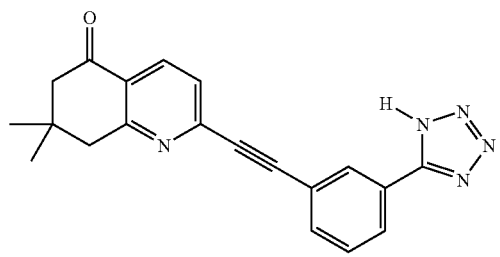

In analogy to the procedure described in Example 1, the title compound is obtained in moderate yield.

EXAMPLE 56

2-[3-(1H-Tetrazol-5-yl)-phenylethynyl]-7,8-dihydro-6H-quinolin-5-one

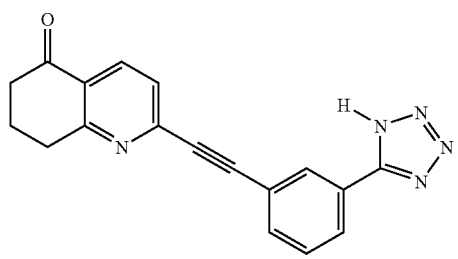

In analogy to the procedure described in Example 1, the title compound is obtained in moderate yield.

EXAMPLE 57

2-[3-Fluoro-5-(1H-tetrazol-5-yl)-phenylethynyl]-6,6-dimethyl-7,8-dihydro-6H-quinolin-5-one

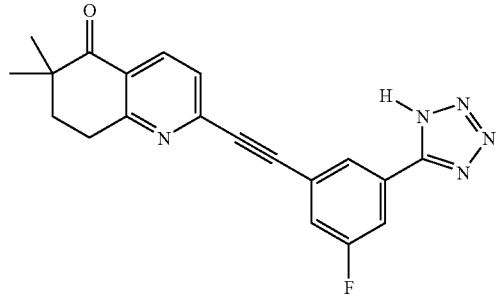

In analogy to the procedure described in Example 1, the title compound is obtained in moderate yield.

EXAMPLE 58

2-[3-Fluoro-5-(1H-tetrazol-5-yl)-phenylethynyl]-7,7-dimethyl-7,8-dihydro-6H-quinolin-5-one

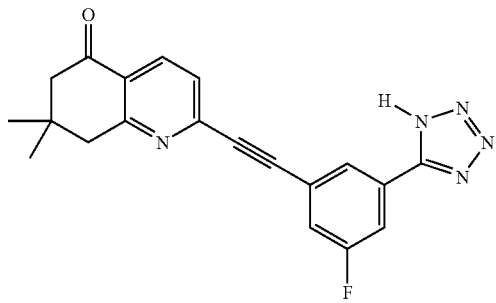

In analogy to the procedure described in Example 1, the title compound is obtained in moderate yield.

EXAMPLE 59

2-[3-Fluoro-5-(1H-tetrazol-5-yl)-phenylethynyl]-7,8-dihydro-6H-quinolin-5-one

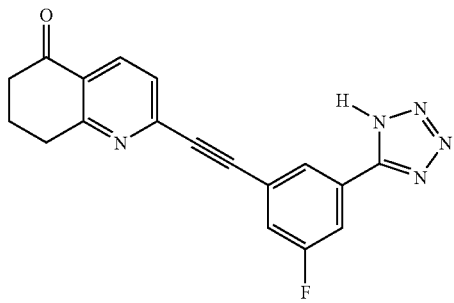

In analogy to the procedure described in Example 1, the title compound is obtained in moderate yield.

EXAMPLE 60

2-(3-Trifluoromethyl-phenylethynyl)-7,8-dihydro-6H-quinolin-5-one

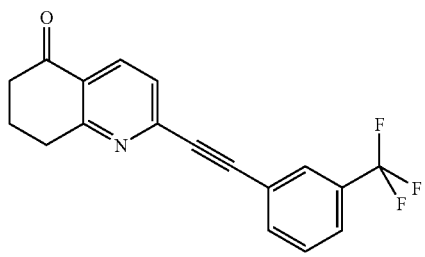

In analogy to the procedure described in Example 1, the title compound is obtained in moderate yield.

EXAMPLE 61

7,7-Dimethyl-2-(3-trifluoromethyl-phenylethynyl)-7,8-dihydro-6H-quinolin-5-one

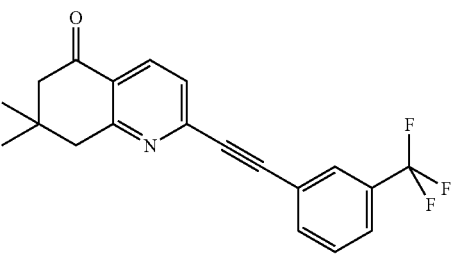

In analogy to the procedure described in Example 1, the title compound is obtained in moderate yield.

EXAMPLE 62

6,6-Dimethyl-2-(3-trifluoromethyl-phenylethynyl)-7,8-dihydro-6H-quinolin-5-one

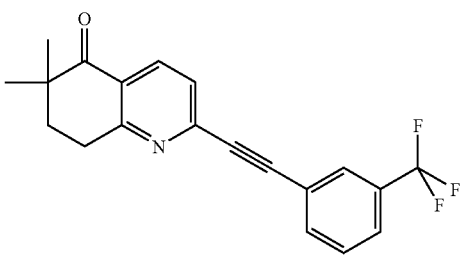

In analogy to the procedure described in Example 1, the title compound is obtained in moderate yield.

EXAMPLE 63

2-(2-Phenyl-thiazol-5-ylethynyl)-7,8-dihydro-6H-quinolin-5-one

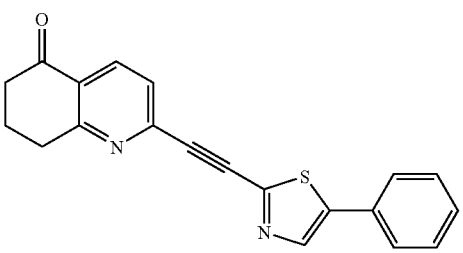

In analogy to the procedure described in Example 1, the title compound is obtained in moderate yield.

EXAMPLE 64

6,6-Dimethyl-2-pyridin-2-ylethynyl-7,8-dihydro-6H-quinolin-5-one

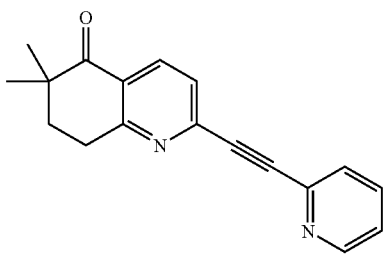

In analogy to the procedure described in Example 1, the title compound is obtained in moderate yield.

EXAMPLE 65

6,6-Dimethyl-2-(4-methyl-oxazol-2-ylethynyl)-7,8-dihydro-6H-quinolin-5-one

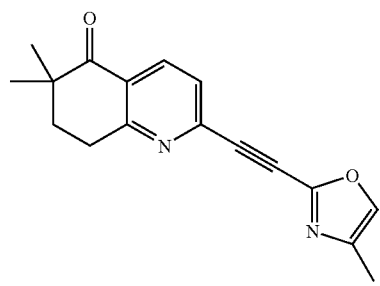

In analogy to the procedure described in Example 1, the title compound is obtained in moderate yield.

EXAMPLE 66

7,7-Dimethyl-2-(4-methyl-oxazol-2-ylethynyl)-7,8-dihydro-6H-quinolin-5-one

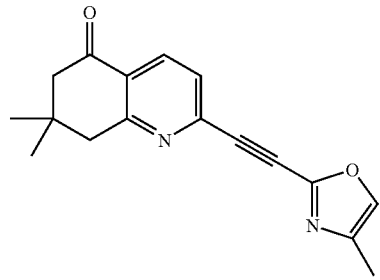

In analogy to the procedure described in Example 1, the title compound is obtained in moderate yield.

EXAMPLE 67

2-(4-Fluoro-5-pyridin-3-yl-1H-imidazol-2-ylethynyl)-7,8-dihydro-6H-quinolin-5-one

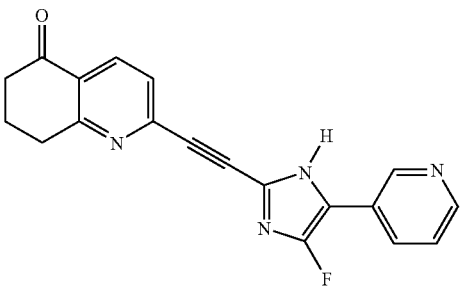

In analogy to the procedure described in Example 1, the title compound is obtained in moderate yield.

EXAMPLE 68

2-(4-Fluoro-5-pyridin-3-yl-1H-imidazol-2-ylethynyl)-7,7-dimethyl-7,8-dihydro-6H-quinolin-5-one

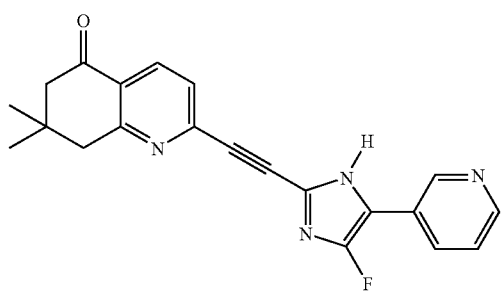

In analogy to the procedure described in Example 1, the title compound is obtained in moderate yield.

EXAMPLE 69

2-(4-Fluoro-5-pyridin-3-yl-1H-imidazol-2-ylethynyl)-6,6-dimethyl-7,8-dihydro-6H-quinolin-5-one

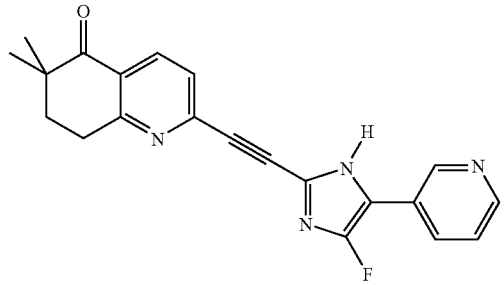

In analogy to the procedure described in Example 1, the title compound is obtained in moderate yield.

EXAMPLE 70

6,6-Dimethyl-2-(4-pyridin-3-yl-imidazol-1-ylethynyl)-7,8-dihydro-6H-quinolin-5-one

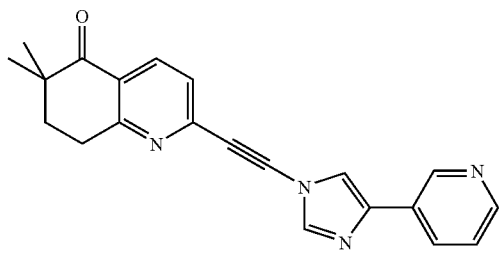

In analogy to the procedure described in Example 1, the title compound is obtained in moderate yield.

EXAMPLE 71

7,7-Dimethyl-2-(4-pyridin-3-yl-imidazol-1-ylethynyl)-7,8-dihydro-6H-quinolin-5-one

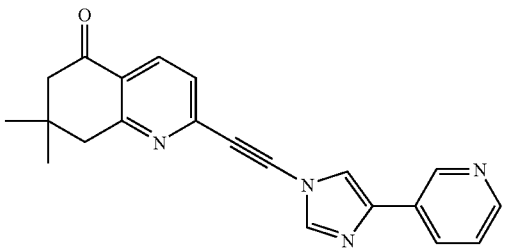

In analogy to the procedure described in Example 1, the title compound is obtained in moderate yield.

EXAMPLE 72

2-(4-Pyridin-3-yl-imidazol-1-ylethynyl)-7,8-dihydro-6H-quinolin-5-one

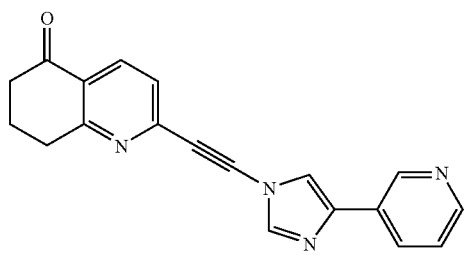

In analogy to the procedure described in Example 1, the title compound is obtained in moderate yield.

EXAMPLE 73

2-[1,3,4]Thiadiazol-2-ylethynyl-7,8-dihydro-6H-quinolin-5-one

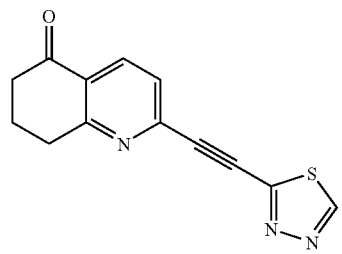

In analogy to the procedure described in Example 1, the title compound is obtained in moderate yield.

EXAMPLE 74

2-[1,3,4]Oxadiazol-2-ylethynyl-7,8-dihydro-6H-quinolin-5-one

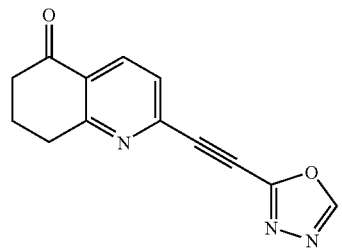

In analogy to the procedure described in Example 1, the title compound is obtained in moderate yield.

EXAMPLE 75

2-(1H-Tetrazol-5-ylethynyl)-7,8-dihydro-6H-quinolin-5-one

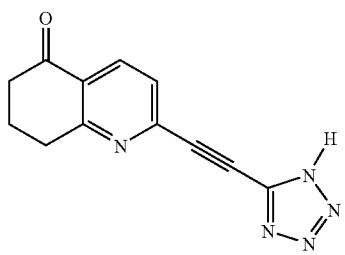

In analogy to the procedure described in Example 1, the title compound is obtained in moderate yield.

EXAMPLE 76

6,6-Dimethyl-2-[1,3,4]thiadiazol-2-ylethynyl-7,8-dihydro-6H-quinolin-5-one

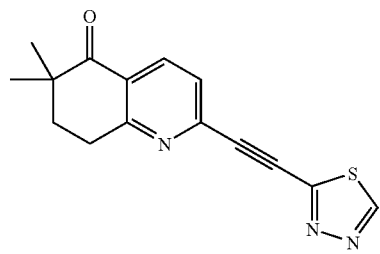

In analogy to the procedure described in Example 1, the title compound is obtained in moderate yield.

EXAMPLE 77

7,7-Dimethyl-2-[1,3,4]thiadiazol-2-ylethynyl-7,8-dihydro-6H-quinolin-5-one

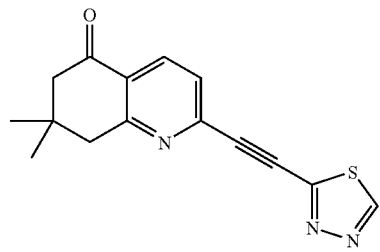

In analogy to the procedure described in Example 1, the title compound is obtained in moderate yield.

EXAMPLE 78

7,7-Dimethyl-2-(1H-tetrazol-5-ylethynyl)-7,8-dihydro-6H-quinolin-5-one

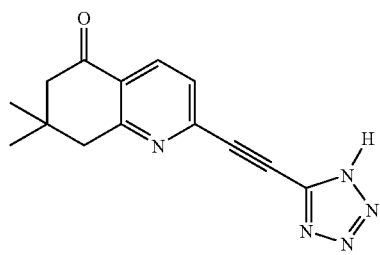

In analogy to the procedure described in Example 1, the title compound is obtained in moderate yield.

EXAMPLE 79

6,6-Dimethyl-2-(1H-tetrazol-5-ylethynyl)-7,8-dihydro-6H-quinolin-5-one

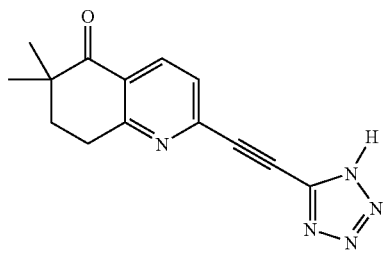

In analogy to the procedure described in Example 1, the title compound is obtained in moderate yield.

EXAMPLE 80

6,6-Dimethyl-2-oxazol-5-ylethynyl-7,8-dihydro-6H-quinolin-5-one

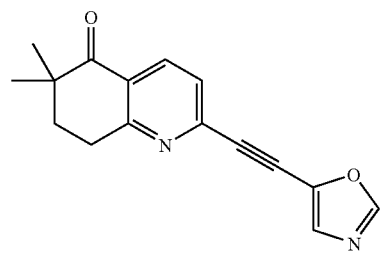

In analogy to the procedure described in Example 1, the title compound is obtained in moderate yield.

EXAMPLE 81

2-Oxazol-2-ylethynyl-7,8-dihydro-6H-quinolin-5-one

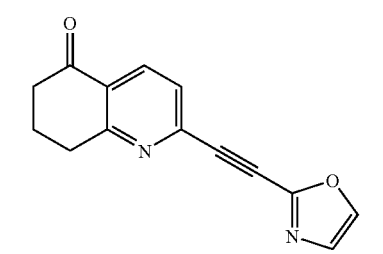

In analogy to the procedure described in Example 1, the title compound is obtained in moderate yield.

EXAMPLE 82

6,6-Dimethyl-2-oxazol-2-ylethynyl-7,8-dihydro-6H-quinolin-5-one

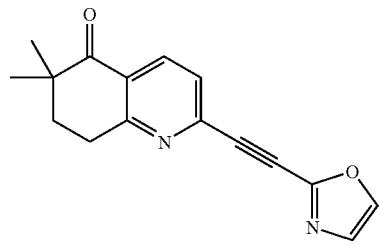

In analogy to the procedure described in Example 1, the title compound is obtained in moderate yield.

EXAMPLE 83

7,7-Dimethyl-2-oxazol-2-ylethynyl-7,8-dihydro-6H-quinolin-5-one

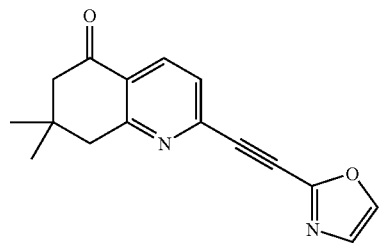

In analogy to the procedure described in Example 1, the title compound is obtained in moderate yield.

EXAMPLE 84

7,7-Dimethyl-2-(2-phenyl-oxazol-5-ylethynyl)-7,8-dihydro-6H-quinolin-5-one

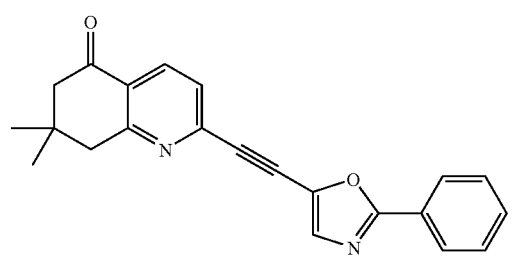

In analogy to the procedure described in Example 1, the title compound is obtained in moderate yield.

EXAMPLE 85

6,6-Dimethyl-2-(2-phenyl-oxazol-5-ylethynyl)-7,8-dihydro-6H-quinolin-5-one

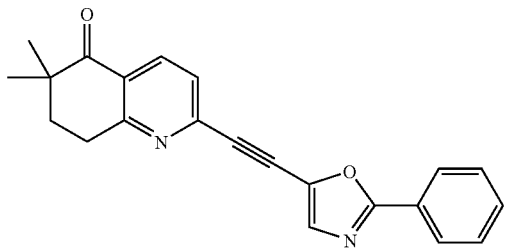

In analogy to the procedure described in Example 1, the title compound is obtained in moderate yield.

EXAMPLE 86

7,7-Dimethyl-2-(5-phenyl-thiazol-2-ylethynyl)-7,8-dihydro-6H-quinolin-5-one

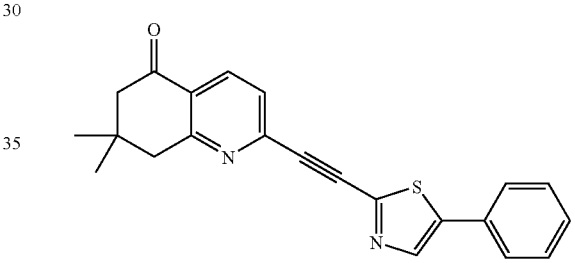

In analogy to the procedure described in Example 1, the title compound is obtained in moderate yield.

EXAMPLE 87

6,6-Dimethyl-2-(5-phenyl-thiazol-2-ylethynyl)-7,8-dihydro-6H-quinolin-5-one

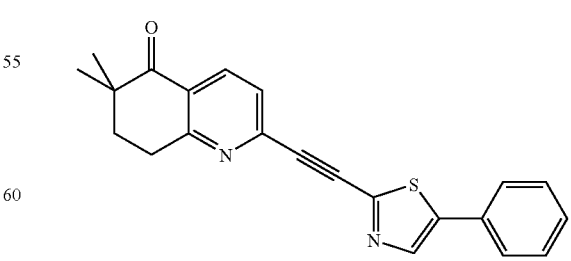

In analogy to the procedure described in Example 1, the title compound is obtained in moderate yield.

EXAMPLE 88

2-(5-Fluoro-pyridin-3-ylethynyl)-6,6-dimethyl-7,8-dihydro-6H-quinolin-5-one

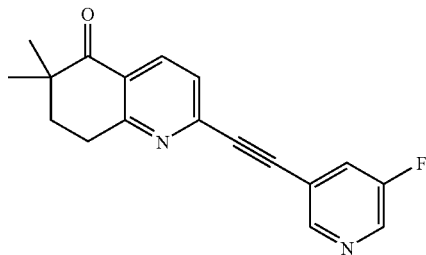

In analogy to the procedure described in Example 1, the title compound is obtained in moderate yield.

EXAMPLE 89

3-Fluoro-5-(5-oxo-5,6,7,8-tetrahydro-quinolin-2-ylethynyl)-benzonitrile

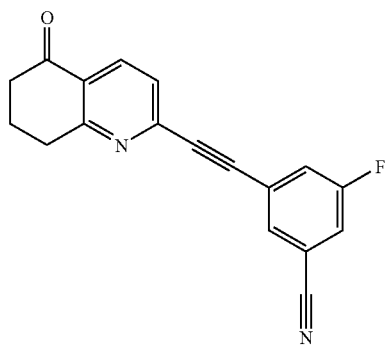

In analogy to the procedure described in Example 1, the title compound is obtained in moderate yield.

EXAMPLE 90

3-(6,6-Dimethyl-5-oxo-5,6,7,8-tetrahydro-quinolin-2-ylethynyl)-5-fluoro-benzonitrile

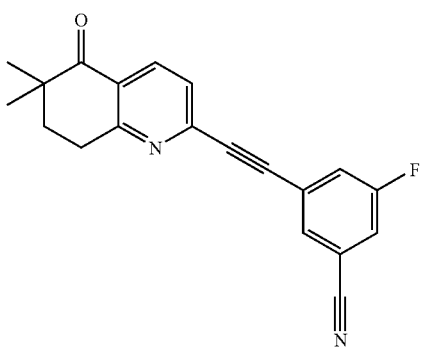

In analogy to the procedure described in Example 1, the title compound is obtained in moderate yield.

EXAMPLE 91

2-(4-Fluoro-5-phenyl-oxazol-2-ylethynyl)-7,7-dimethyl-7,8-dihydro-6H-quinolin-5-one

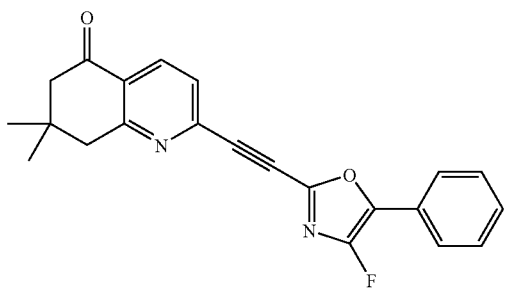

In analogy to the procedure described in Example 1, the title compound is obtained in moderate yield.

EXAMPLE 92

2-(4-Fluoro-5-phenyl-oxazol-2-ylethynyl)-6,6-dimethyl-7,8-dihydro-6H-quinolin-5-one

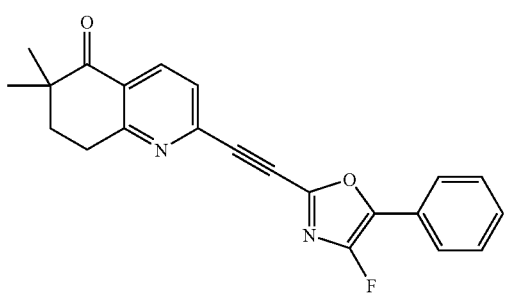

In analogy to the procedure described in Example 1, the title compound is obtained in moderate yield.

EXAMPLE 93

6,6-Dimethyl-2-(5-pyridin-3-yl-[1,3,4]oxadiazol-2-ylethynyl)-7,8-dihydro-6H-quinolin-5-one

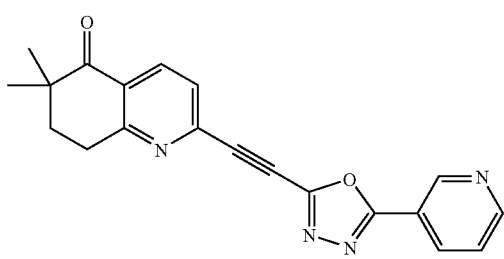

In analogy to the procedure described in Example 1, the title compound is obtained in moderate yield.

EXAMPLE 94

7,7-Dimethyl-2-(5-pyridin-3-yl-[1,3,4]oxadiazol-2-ylethynyl)-7,8-dihydro-6H-quinolin-5-one

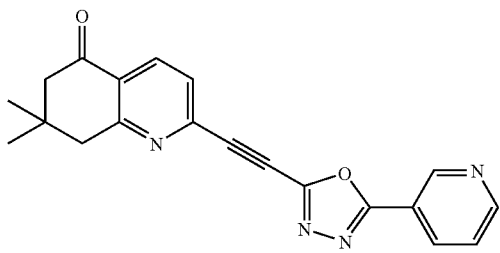

In analogy to the procedure described in Example 1, the title compound is obtained in moderate yield.

EXAMPLE 95

2-(5-Pyridin-3-yl-[1,3,4]oxadiazol-2-ylethynyl)-7,8-dihydro-6H-quinolin-5-one

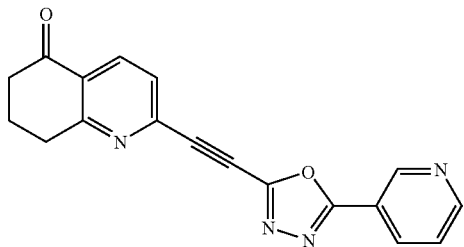

In analogy to the procedure described in Example 1, the title compound is obtained in moderate yield.

EXAMPLE 96

7,7-Dimethyl-2-phenylethynyl-7,8-dihydro-6H-quinolin-5-one

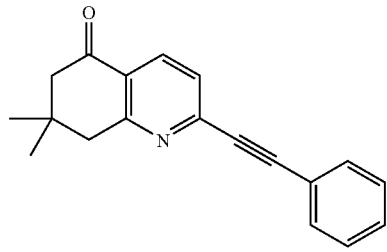

In analogy to the procedure described in Example 1, the title compound is obtained in moderate yield.

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers may be separated from each other by selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric form of appropriate starting materials, provided that the reaction occurs stereoselectively. Stereoisomeric forms of Formula I are obviously intended to be included within the scope of this invention.

Addition Salts

For therapeutic use, salts of the compounds of Formula I are those wherein the counterion is pharmaceutically acceptable. However, salts of acids and bases which are non-pharmaceutically acceptable may also find use, for example, in the preparation and purification of pharmaceutically acceptable compounds. All salts whether pharmaceutically acceptable or not are included within the ambit of the present invention. The pharmaceutically acceptable salts as mentioned above are meant to comprise the therapeutically active non-toxic salt forms which the compounds of Formula I are able to form. The latter can conveniently be obtained by treating the base form with such appropriate acids as inorganic acids, e.g. hydrohalic acids such as hydrochloric, hydrobromic and the like; sulfuric acid; nitric acid; phosphoric acid and the like; or organic acids such as acetic, propanoic, hydroxyacetic, 2-hydroxypropanoic, oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely, the salt form can be converted by treatment with alkali into the free base form.

Pharmaceutical Compositions

The active ingredients of the invention, together with one or more conventional adjuvants, carriers, or diluents, may be placed into the form of pharmaceutical compositions and unit dosages thereof, and in such form may be employed as solids, such as coated or uncoated tablets or filled capsules, or liquids, such as solutions, suspensions, emulsions, elixirs, or capsules filled with the same, all for oral use; in the form of suppositories or capsules for rectal administration or in the form of sterile injectable solutions for parenteral (including intravenous or subcutaneous) use. Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing one (1) to one hundred (100) milligrams of active ingredient or, more broadly, zero point five (0.5) to five hundred (500) milligrams per tablet, are accordingly suitable representative unit dosage forms.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18$^{th}$ Edition.

Method of Treating

Due to their high degree of activity and their low toxicity, together presenting a most favorable therapeutic index, the active principles of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous and subcutaneous) or in some cases even topical route, in an effective amount. Suitable dosage ranges are 1-1000 milligrams daily, preferably 10-500 milligrams daily, and especially 50-500 milligrams daily, depending as usual upon the exact mode of administration, form in which administered, the indication toward which the administration is directed, the subject involved and the body weight of the subject involved, and the preference and experience of the physician or veterinarian in charge.

The term "therapeutically effective" applied to dose or amount refers to that quantity of a compound or pharmaceutical composition that is sufficient to result in a desired activity upon administration to a living animal body in need thereof.

The active agents of the present invention may be administered orally, topically, parenterally, or mucosally (e.g., buccally, by inhalation, or rectally) in dosage unit formulations containing conventional non-toxic pharmaceutically acceptable carriers. It is usually desirable to use the oral route. The active agents may be administered orally in the form of a capsule, a tablet, or the like (see Remington: The Science and Practice of Pharmacy, $20^{th}$ Edition (2000), Philadelphia, Pa.). The orally administered medicaments may be administered in the form of a time-controlled release vehicle, including diffusion-controlled systems, osmotic devices, dissolution-controlled matrices, and erodible/degradable matrices.

For oral administration in the form of a tablet or capsule, the active drug component can be combined with a non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like. For oral administration in liquid form, the drug components can be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) can also be added to stabilize the dosage forms.

The tablets can be coated by methods well known in the art. The compositions of the invention can be also introduced in microspheres or microcapsules, e.g., fabricated from polyglycolic acid/lactic acid (PGLA). Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known.

Drugs of the invention may also be delivered by the use of monoclonal antibodies as individual carriers to which the compound molecules are coupled. Active drugs may also be coupled with soluble polymers as targetable drug carriers. Such polymers can include polyvinyl-pyrrolidone, pyran copolymer, polyhydroxy-propyl methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

For administration by inhalation, the therapeutics according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The formulations of the invention can be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

Compositions of the present invention can also be formulated for rectal administration, e.g., as suppositories or retention enemas (e.g., containing conventional suppository bases such as cocoa butter or other glycerides).

The compositions may, if desired, be presented in a pack or dispenser device which may contain one or more unit dosage forms containing the active ingredient and/or may contain different dosage levels to facilitate dosage titration. The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

EXAMPLES OF REPRESENTATIVE PHARMACEUTICAL COMPOSITIONS

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions follow.

(a) Tablets suitable for oral administration which contain the active ingredient may be prepared by conventional tabletting techniques.
(b) For suppositories, any usual suppository base may be employed for incorporation thereinto by usual procedure of the active ingredient, such as a polyethyleneglycol which is a solid at normal room temperature but which melts at or about body temperature.
(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

FORMULATION EXAMPLES

The following examples are again given by way of illustration only and are not to be construed as limiting.

Example 1

Tablet Formulation

A suitable formulation for a tablet containing 10 milligrams of active ingredient is as follows:

|  | mg |
|---|---|
| Active Ingredient | 10 |
| Lactose | 61 |
| Microcrystalline Cellulose | 25 |
| Talcum | 2 |
| Magnesium stearate | 1 |
| Colloidal silicon dioxide | 1 |

Example 2

Tablet Formulation

Another suitable formulation for a tablet containing 100 mg is as follows:

|  | mg |
|---|---|
| Active Ingredient | 100 |
| Polyvinylpyrrolidone, crosslinked | 10 |
| Potato starch | 20 |
| Polyvinylpyrrolidone | 19 |
| Magnesium stearate | 1 |
| Microcrystalline Cellulose | 50 |
| Film coated and colored. | |
| The film coating material consists of: | |
| Hypromellose | 10 |
| Microcryst. Cellulose | 5 |
| Talcum | 5 |
| Polyethylene glycol | 2 |
| Color pigments | 5 |

Example 3

Capsule Formulation

A suitable formulation for a capsule containing 50 milligrams of active ingredient is as follows:

|  | mg |
|---|---|
| Active Ingredient | 50 |
| Corn starch | 26 |
| Dibasic calcium phosphate | 50 |
| Talcum | 2 |
| Colloidal silicon dioxide | 2 | filled in a gelatin capsule.

Example 4

Solution for Injection

A suitable formulation for an injectable solution is as follows:

| Active Ingredient | mg | 10 |
|---|---|---|
| Sodium chloride | mg | q.s. |
| Water for Injection | mL | add 1.0 |

Example 5

Liquid Oral Formulation

A suitable formulation for 1 liter of a an oral solution containing 2 milligrams of active ingredient in one milliliter of the mixture is as follows:

|  | mg |
| --- | --- |
| Active Ingredient | 2 |
| Saccharose | 250 |
| Glucose | 300 |
| Sorbitol | 150 |
| Orange flavor | 10 |
| Colorant | q.s. |
| Purified water | add 1000 mL |

Example 6

Liquid Oral Formulation

Another suitable formulation for 1 liter of a liquid mixture containing 20 milligrams of active ingredient in one milliliter of the mixture is as follows:

|  | G |
| --- | --- |
| Active Ingredient | 20.00 |
| Tragacanth | 7.00 |
| Glycerol | 50.00 |
| Saccharose | 400.00 |
| Methylparaben | 0.50 |
| Propylparaben | 0.05 |
| Black currant-flavor | 10.00 |
| Soluble Red color | 0.02 |
| Purified water | add 1000 mL |

Example 7

Liquid Oral Formulation

Another suitable formulation for 1 liter of a liquid mixture containing 2 milligrams of active ingredient in one milliliter of the mixture is as follows:

|  | G |
| --- | --- |
| Active Ingredient | 2 |
| Saccharose | 400 |
| Bitter orange peel tincture | 20 |
| Sweet orange peel tincture | 15 |
| Purified water | add 1000 mL |

Example 8

Aerosol Formulation 180 g aerosol solution contain:

|  | G |
| --- | --- |
| Active Ingredient | 10 |
| Oleic acid | 5 |
| Ethanol | 81 |
| Purified Water | 9 |
| Tetrafluoroethane | 75 |

15 ml of the solution are filled into aluminum aerosol cans, capped with a dosing valve, purged with 3.0 bar.

Example 9

TDS Formulation 100 g solution contain:

|  | G |
| --- | --- |
| Active Ingredient | 10.0 |
| Ethanol | 57.5 |
| Propyleneglycol | 7.5 |
| Dimethylsulfoxide | 5.0 |
| Hydroxyethylcellulose | 0.4 |
| Purified water | 19.6 |

1.8 ml of the solution are placed on a fleece covered by an adhesive backing foil. The system is closed by a protective liner which will be removed before use.

Example 10

Nanoparticle Formulation 10 g of polybutylcyanoacrylate nanoparticles contain:

|  | G |
| --- | --- |
| Active Ingredient | 1.00 |
| Poloxamer | 0.10 |
| Butylcyanoacrylate | 8.75 |
| Mannitol | 0.10 |
| Sodium chloride | 0.05 |

Polybutylcyanoacrylate nanoparticles are prepared by emulsion polymerization in a water/0.1 N HCl/ethanol mixture as polymerizsation medium. The nanoparticles in the suspension are finally lyophilized under vacuum.

Pharmacology—Summary

The active principles of the present invention, and pharmaceutical compositions thereof and method of treating therewith, are characterized by unique and advantageous properties, rendering the "subject matter as a whole", as claimed herein, unobvious. The compounds and pharmaceutical compositions thereof exhibit, in standard accepted reliable test procedures, the following valuable properties and characteristics:

Methods

Binding Assays for the Characterization of mGluR5 Antagonist Properties

[$^3$H]MPEP (2-methyl-6-(phenylethynyl)pyridine) binding to transmembrane allosteric modulatory sites of mGluR5 receptors in cortical membranes Preparation of Rat Cortical Membranes:

Male Sprague-Dawley rats (200-250 g) are decapitated and their brains are removed rapidly. The cortex is dissected and homogenized in 20 volumes of ice-cold 0.32 M sucrose using a glass-Teflon homogenizer. The homogenate is centrifuged at 1000×g for 10 min. The pellet is discarded and the supernatant centrifuged at 20,000×g for 20 min. The resulting pellet is re-suspended in 20 volumes of distilled water and centrifuged for 20 min at 8000×g. Then the supernatant and the buffy coat are centrifuged at 48,000×g for 20 min in the presence of 50 mM Tris-HCl, pH 8.0. The pellet is then re-suspended and centrifuged two to three more times at 48,000×g for 20 min in the presence of 50 mM Tris-HCl, pH 8.0. All centrifugation steps are carried out at 4° C. After resuspension in 5 volumes of 50 mM Tris-HCl, pH 8.0 the membrane suspension is frozen rapidly at −80° C.

On the day of assay the membranes are thawed and washed four times by resuspension in 50 mM Tris-HCl, pH 8.0 and centrifugation at 48,000×g for 20 min. and finally re-suspended in 50 mM Tris-HCl, pH 7.4. The amount of protein in the final membrane preparation (250-500 µg/ml) is determined according to the method of Lowry (Lowry O. H. et al., 1951. J. Biol. Chem. 193, 256-275).

[$^3$H]MPEP Assay

Incubations are started by adding ($^3$H)-MPEP (50.2 Ci/mmol, 5 nM, Tocris) to vials with 125-250 µg protein (total volume 0.5 ml) and various concentrations of the agents. The incubations are continued at room temperature for 60 min (equilibrium was achieved under the conditions used). Non-specific binding is defined by the addition of unlabeled MPEP (10 µM). Incubations are terminated using a Millipore filter system. The samples are rinsed twice with 4 ml of ice cold assay buffer over glass fibre filters (Schleicher & Schuell) under a constant vacuum. Following separation and rinse, the filters are placed into scintillation liquid (5 ml Ultima Gold) and radioactivity retained on the filters is determined with a conventional liquid scintillation counter (Hewlett Packard, Liquid Scintillation Analyser).

Characterization

Specific binding is extremely high i.e. normally >85% and essentially independent of buffer (Tris or HEPES oth 50 mM) and pH (6.8-8.9). There is a clear saturable protein dependence and the chosen protein concentration used for subsequent assays (250-500 µg/ml) is within the linear portion of this dependence. Cold MPEP displaces hot ligand with an $IC_{50}$ of 18.8±4.1 nM. The Kd of ($^3$H)-MPEP of 13.6 nM is determined by Scatchard analysis and used according to the Cheng Prussoff relationship to calculate the affinity of displacers as Kd values ($IC_{50}$ of cold MPEP equates to a Ki of 13.7 nM). $B_{max}$ was 0.56 pm/mg protein. Compounds of the present invention exhibit specific affinity for transmembrane modulatory sites of mGLuR5 receptors in cortical/cerebellar membrane preparations.

Functional Assay of MGLUR5 Receptors

Materials and Methods

Astrocyte Culture

Primary astrocyte cultures were prepared from cortices of newborn rats as described by Booher and Sensenbrenner (1972). Briefly, Sprague-Dawley rat pups (2-4 d old) were decapitated and neocortices were dissected, disintegrated with a nylon filter (poresize 80 µm) and carefully triturated. The cell suspension was plated on poly-D-lysine precoated flasks (Costar) and cultivated in Dulbecco's Modified Eagle's Medium (DMEM, InVitrogen) supplemented with 10% heat inactivated fetal calf serum ($FCS_i$, Sigma), 4 mM glutamine (Biochrom) and 50 µg/mL gentamycin (Biochrom) at 37° C. in a humidified atmosphere of 5% $CO_2$/95% air for 7 d with exchanging the medium at day 2.

After 7 DIV, cells were shaken overnight at 250 rpm to remove oligodendrocytes and microglia. The next day, astrocytes were rinsed twice with CMF-PBS, trypsinized and sub-plated on poly-D-lysine precoated 96-well plates (Becton Dickinson #6516 or #6640) at a density of 40,000-45,000 cells/well. 24 h after establishing the secondary culture the astrocytes were rinsed with PBS$^{++}$ and fed with astrocyte-defined medium (ADM) consisting of DMEM containing 1×G5-supplement (InVitrogen), 0.5 µg/mL heparan sulfate (Sigma), and 1.5 µg/mL fibronectin (Sigma) (Miller et al., 1993). 3 d later the medium was exchanged and the cells incubated for another 2-3 d, so that at the time of experiments astrocytes were 14-15 DIV.

Immunocytochemistry

Immunostaining was performed to confirm the presence of classical astrocytic markers such as GFAP as well the expression of mGluR5 receptors.

Accumulation of [$^3$H]-Inositol Phosphates

After astrocytes were cultured for 12 d ADM was removed and inositol-free DMEM (MP Biomedicals) supplemented with [$^3$H]myo-inositol (0.5 µCi/well; Perkin Elmer), and the ADM chemicals was added. After 48 h the medium was replaced with 100 µL Locke's buffer (plus 20 mM Li$^+$, pH 7.4) and incubated for 15 min at 37° C. before replacement with agonists/antagonists in Locke's buffer. The incubation (45 min at 37° C.) was terminated by replacing the Locke's solutions with 100 µL 0.1 M HCl (10 min on ice). The 96 well plates can be frozen at −20° C. at this stage until further analysis. Home made resin exchange columns (AG1-X8 Biorad, 140-14444) were used to separate labeled inositol phosphates by elution with 1 mL of 1 M ammonium formate/0.1 M formic acid into 24-well visiplates (Perkin Elmer). Scintillation liquid (UltimaFlow AF, Perkin Elmer) was added, the plate sealed and vortexed before radioactivity was determined by conventional liquid scintillation counting (Microbeta, Perkin Elmer) as disintegration per minute (DPM).

Calcium FLIPR Studies

Cultured astrocytes expressed mGluR5 receptors as shown by immunostaining. The increase of intracellular calcium after stimulation with the mGluR5 agonist DHPG or L-quisqualate was measured using the fluorometric imaging plate reader (FLIPR) and the Ca-Kit (both Molecular Devices, CA). Prior to addition of agonist or antagonist the medium was aspirated and cells were loaded for 2 h at RT with 150 µL of loading buffer consisting of Ca-sensitive dye (MD # R8033) reconstituted in sodium chloride (123 mM), potassium chloride (5.4 mM), magnesium chloride (0.8 mM), calcium chloride (1.8 mM), D-glucose (15 mM), and HEPES (20 mM), pH 7.3. Subsequently, plates were transferred to FLIPR to detect calcium increase with the addition of DHPG (300 µM) or L-quisqualate (100 nM) measured as relative fluorescence units (RFU). If antagonists were tested, these compounds were pre-incubated for 10 min at RT before addition of the respective agonist.

For positive modulators, concentration-response curves for quisqualate were performed in the presence and absence of 10 µM modulator to determine the extent of potentiation/agonist potency increase. Thereafter, concentration-response curves for the positive modulator were performed in the presence of a fixed concentration of quisqualate showing the biggest window for potentiation (normally 10-30 nM).

Data Analysis

The fluorescence signal increase after addition of agonist reflects the increase of intracellular calcium. Inconsistencies in the amount of cells per well were normalised by using the spatial uniformity correction of the FLIPR software. The mean of replicated temporal data (n=5) was calculated and used for graphical representation. For the evaluation of the pharmacology, the calcium changes in response to different concentrations of agonist or antagonist were determined using a maximum minus minimum (MaxMin) calculation.

All responses (DPM- or RFU-values) were determined as percentage of control (=maximum response at 100 nM quisqualate).

$EC_{50}$ and $IC_{50}$ were calculated according the logistic equation using GraFit 5.0 (Erithacus Software).

Chemicals

Unless otherwise stated all chemicals were purchased from Sigma.

REFERENCES

Booher and Sensenbrenner (1972) *Neurobiology* 2(3):97-105
Miller et al., (1993) *Brain Res.* 618(1):175-8

Compounds of the present invention have an EC50 range of about 0.5 nM to about 100 μM.

CONCLUSIONS

In conclusion, from the foregoing, it is apparent that the present invention provides novel, valuable, and unpredictable applications and uses of the compounds of the present invention, which compounds comprise the active principle according to the present invention, as well as novel pharmaceutical compositions thereof and methods of preparation thereof and of treating therewith, all possessed of the foregoing more specifically-enumerated characteristics and advantages.

The high order of activity of the active agent of the present invention and compositions thereof, as evidenced by the tests reported, is indicative of utility based on its valuable activity in human beings as well as in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug Administration, which are responsible for and authorized to pass judgment on such questions.

The instant ethynyl-substituted tetrahydroquinolinone derivatives represent a novel class of Group I mGluR modulators. They are especially useful as mGluR 5 positve modulators or agonists. In view of their potency, they will be useful therapeutics in a wide range of CNS disorders which involve abnormal glutamate induced excitation.

These compounds accordingly find application in the treatment of the following disorders of a living animal body, especially a human: AIDS-related dementia, Alzheimer's disease, Creutzfeld-Jakob's syndrome, bovine spongiform encephalopathy (BSE) or other prion related infections, diseases involving mitochondrial dysfunction, diseases involving β-amyloid and/or tauopathy such as Down's syndrome, hepatic encephalopathy, Huntington's disease, motor neuron diseases such as amyotrophic lateral sclerosis (ALS), multiple sclerosis (MS), olivoponto-cerebellar atrophy, post-operative cognitive deficit (POCD), Parkinson's disease, Parkinson's dementia, mild cognitive impairment, dementia pugilisitca, vascular and frontal lobe dementia, cognitive impairment, eye injuries or diseases (e.g. glaucoma, retinopathy, macular degeneration), head and spinal cord injuries/trauma, hypoglycaemia, hypoxia (e.g. perinatal), ischaemia (e.g. resulting from cardiac arrest, stroke, bypass operations or transplants), convulsions, glioma and other tumours, inner ear insult (e.g. in tinnitus, sound or drug-induced), L-dopa-induced and tardive dyskinesias.

These compounds also find application in the treatment of the following disorders of a living animal body, especially a human: addiction (nicotine, alcohol, opiate, cocaine, amphetamine obesity and others), amyotrophic lateral sclerosis (ALS), anxiety and panic disorders, attention deficit hyperactivity disorder (ADHD), restless leg syndrome, hyperactive children, autism, convulsions/epilepsy, dementia (e.g. in Alzheimer's disease, Korsakoff syndrome, vascular dementia, HIV infections), major depressive disorder or depression (including that resulting from Borna virus infection) and bipolar manic-depressive disorder, drug tolerance e.g. to opioids, movement disorders, dystonia, dyskinesia (e.g. L-Dopa-induced, tardive dyskinesia or in Huntington's disease), fragile-X syndrome, Huntington's chorea, irritable bowel syndrome (IBS), migraine, multiple sclerosis, muscle spasms, pain (chronic and acute, e.g. inflammatory pain, neuropathic pain, allodynia, hyperalgesia, nociceptive pain), Parkinson's disease, post traumatic stress disorder, schizophrenia (positive and negative symptoms), spasticity, tinnitus, Tourette's syndrome, urinary incontinence and vomiting, pruritic conditions (e.g. pruritis), sleep disorders, micturition disorders, neuromuscular disorder in the lower urinary tract, gastroesophageal reflux disease (GERD), lower esophageal sphincter (LES) disease, functional gastrointestinal disorders, dyspepsia, regurgitation, respiratory tract infection, bulimia nervosa, chronic laryngitis, asthma (e.g. reflux-related asthma), lung disease, eating disorders, obesity and obesity-related disorders.

These compounds also find application in the treatment of indications in of a living animal body, especially a human, wherein a particular condition does not necessarily exist but wherein a particular physiological parameter may be improved through administration of the instant compounds, including cognitive enhancement.

The method-of-treating a living animal body with a compound of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the compounds of the present invention in the manufacture of a medicament for the treatment of a living animal for inhibition of progression or alleviation of selected ailments or conditions, particularly ailments or conditions susceptible to treatment with a Group I mGluR modulator, in particular an mGluR 5 modulator, especially an mGluR 5 positive modulator or agonist, is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active ingredient with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or dermal use, also in accord with the foregoing.

The present invention is not to be limited in scope by the specific embodiments described herein. Indeed, various modifications of the invention in addition to those described herein will become apparent to those skilled in the art from the foregoing description.

The invention claimed is:

1. A compound selected from those of Formula I $$\text{[Structure I]}$$

wherein
$R^1$ represents aryl or heteroaryl;
$R^2$ and $R^3$, which may be the same or different, represent hydrogen or $C_{1-6}$alkyl;
$R^4$ and $R^5$, which may be the same or different, represent hydrogen or $C_{1-6}$alkyl;
it being understood that:
aryl represents an unsubstituted phenyl ring or a phenyl ring that is substituted with 1, 2, 3, 4 or 5 substituents, that may be the same or different, which substituents are selected from $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$alkylamino, N-cyclo$C_{3-12}$alkyl-N-$C_{1-6}$alkylamino, azetidinyl, pyrrolidinyl, piperidinyl, morpholinyl, 4-$C_{1-6}$alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
heteroaryl represents a (hetero)aromatic 5-, 6- or 7-membered ring having from 1 to 4 heteroatoms, said heteroatoms being independently selected from oxygen, nitrogen and sulfur, wherein said ring is unsubstituted or substituted with 1, 2 or 3 substituents, that may be the same or different, which substituents are selected from $C_{1-6}$alkyl, which is optionally substituted with one or more fluorine, chlorine or bromine atoms, $C_{1-6}$alkoxy, which is optionally substituted with one or more fluorine, chlorine or bromine atoms, cyclo$C_{3-12}$alkyl, hydroxyl, F, Cl, Br, I, CN, nitro, di-$C_{1-6}$alkylamino, N-cyclo$C_{3-12}$alkyl-N—$C_{1-6}$alkylamino, azetidinyl, pyrrolidinyl, piperidinyl, morpholinyl, 4-$C_{1-6}$alkyl-piperazinyl, tetrazolyl, oxazolyl, furyl, thiophenyl, pyrrolyl, isoxazolyl, thiazolyl, imidazolyl, oxadiazolyl, pyridinyl, pyrimidyl, and phenyl;
and optical isomers and pharmaceutically acceptable salts thereof.

2. The compound of claim 1, wherein
$R^2$ and $R^3$, which may be the same or different, represent methyl, ethyl, n-propyl, 2-propyl, n-butyl, tert-butyl and
$R^4$ and $R^5$ represent hydrogen.

3. The compound of claim 1, wherein
$R^2$ and $R^3$ represent hydrogen and
$R^4$ and $R^5$, which may be the same or different, represent methyl, ethyl, n-propyl, 2-propyl, n-butyl, tert-butyl.

4. The compound of claim 1, wherein
$R^2$, $R^3$, $R^4$ and $R^5$, which may be the same or different represent hydrogen, methyl or ethyl.

5. The compound of claim 1, wherein
$R^1$ represents aryl;
it being understood that:
aryl represents unsubstituted phenyl or phenyl which is mono- or di-substituted with the same or different substituents which are selected from methyl, ethyl, n-propyl, 2-propyl, n-butyl, tert-butyl, hydroxyl, methoxy, ethoxy, n-propoxy, iso-propoxy, n-butoxy, tert-butoxy, $CF_3$, $CH_2F$, $CH_2F$, $C_2F_5$, $OCF_3$, $OC_2F_5$, F, Cl, Br, CN, piperidinyl, morpholinyl, tetrazolyl, oxazolyl, furyl, thiophenyl, pyrrolyl, isoxazolyl, thiazolyl, imidazolyl, oxadiazolyl, pyridinyl, pyrimidyl, and phenyl.

6. The compound of claim 5, wherein
aryl represents unsubstituted phenyl or phenyl that is mono- or di-substituted bearing substituent(s) in the meta-position.

7. The compound of claim 1, wherein
$R^1$ represents heteroaryl;
it being understood that:
heteroaryl represents pyridin-2-yl, pyridin-3-yl, pyridin-4-yl, oxazol-5-yl, thiazol-5-yl, wherein each of these rings may be unsubstituted or mono or di-substituted with phenyl, methyl, ethyl, n-propyl, 2-propyl, n-butyl, tert-butyl, hydroxyl, methoxy, ethoxy, n-propoxy, iso-propoxy, n-butoxy, tert-butoxy, $CF_3$, $CH_2F$, $CH_2F$, $C_2F_5$, $OCF_3$, $OC_2F_5$, F, Cl, Br, CN, piperidinyl, morpholinyl, tetrazolyl, oxazolyl, furyl, thiophenyl, isoxazolyl, thiazolyl, imidazolyl, oxadiazolyl, pyridinyl, and/or pyrimidyl.

8. The compound of claim 1 which is selected from:
2-Phenylethynyl-7,8-dihydro-6H-quinolin-5-one,
2-Pyridin-3-ylethynyl-7,8-dihydro-6H-quinolin-5-one,
2-m-Tolylethynyl-7,8-dihydro-6H-quinolin-5-one,
2-(3-Hydroxy-phenylethynyl)-7,8-dihydro-6H-quinolin-5-one,
2-(3-Methoxy-phenylethynyl)-7,8-dihydro-6H-quinolin-5-one,
2-(3-Fluoro-phenylethynyl)-7,8-dihydro-6H-quinolin-5-one,
2-(3-Chloro-phenylethynyl)-7,8-dihydro-6H-quinolin-5-one,
2-(3-Bromo-phenylethynyl)-7,8-dihydro-6H-quinolin-5-one,
3-(5-Oxo-5,6,7,8-tetrahydro-quinolin-2-ylethynyl)-benzonitrile,
2-Thiazol-5-ylethynyl-7,8-dihydro-6H-quinolin-5-one,
2-Oxazol-5-ylethynyl-7,8-dihydro-6H-quinolin-5-one,
7,7-Dimethyl-2-pyridin-3-ylethynyl-7,8-dihydro-6H-quinolin-5-one,
7,7-Dimethyl-2-m-tolylethynyl-7,8-dihydro-6H-quinolin-5-one,
2-(3-Hydroxy-phenylethynyl)-7,7-dimethyl-7,8-dihydro-6H-quinolin-5-one,
2-(3-Methoxy-phenylethynyl)-7,7-dimethyl-7,8-dihydro-6H-quinolin-5-one,
2-(3-Fluoro-phenylethynyl)-7,7-dimethyl-7,8-dihydro-6H-quinolin-5-one,
2-(3-Chloro-phenylethynyl)-7,7-dimethyl-7,8-dihydro-6H-quinolin-5-one,
2-(3-Bromo-phenylethynyl)-7,7-dimethyl-7,8-dihydro-6H-quinolin-5-one,
3-(7,7-Dimethyl-5-oxo-5,6,7,8-tetrahydro-quinolin-2-ylethynyl)-benzonitrile,
7,7-Dimethyl-2-thiazol-5-ylethynyl-7,8-dihydro-6H-quinolin-5-one,
7,7-Dimethyl-2-oxazol-5-ylethynyl-7,8-dihydro-6H-quinolin-5-one, 2-(2-Phenyl-oxazol-5-ylethynyl)-7,8-dihydro-6H-quinolin-5-one,
2-(2-Phenyl-thiazol-5-ylethynyl)-7,8-dihydro-6H-quinolin-5-one,
2-Pyridin-2-ylethynyl-7,8-dihydro-6H-quinolin-5-one,
7,7-Dimethyl-2-pyridin-2-ylethynyl-7,8-dihydro-6H-quinolin-5-one,
6,6-Dimethyl-2-pyridin-3-ylethynyl-7,8-dihydro-6H-quinolin-5-one,
2-(3-Fluoro-phenylethynyl)-6,6-dimethyl-7,8-dihydro-6H-quinolin-5-one,
2-(3-Chloro-phenylethynyl)-6,6-dimethyl-7,8-dihydro-6H-quinolin-5-one,
2-(3-Methoxy-phenylethynyl)-6,6-dimethyl-7,8-dihydro-6H-quinolin-5-one,
2-(3-Hydroxy-phenylethynyl)-6,6-dimethyl-7,8-dihydro-6H-quinolin-5-one,
3-(6,6-Dimethyl-5-oxo-5,6,7,8-tetrahydro-quinolin-2-ylethynyl)-benzonitrile,
6,6-Dimethyl-2-thiazol-5-ylethynyl-7,8-dihydro-6H-quinolin-5-one,
6,6-Dimethyl-2-(3-piperidin-1-yl-phenylethynyl)-7,8-dihydro-6H-quinolin-5-one,
7,7-Dimethyl-2-(3-piperidin-1-yl-phenylethynyl)-7,8-dihydro-6H-quinolin-5-one,
2-(3-Piperidin-1-yl-phenylethynyl)-7,8-dihydro-6H-quinolin-5-one,
2-(3-Morpholin-4-yl-phenylethynyl)-7,8-dihydro-6H-quinolin-5-one,
7,7-Dimethyl-2-(3-morpholin-4-yl-phenylethynyl)-7,8-dihydro-6H-quinolin-5-one,
6,6-Dimethyl-2-(3-morpholin-4-yl-phenylethynyl)-7,8-dihydro-6H-quinolin-5-one,
6,6-Dimethyl-2-[3-(1H-tetrazol-5-yl)-phenylethynyl]-7,8-dihydro-6H-quinolin-5-one,
7,7-Dimethyl-2-[3-(1H-tetrazol-5-yl)-phenylethynyl]-7,8-dihydro-6H-quinolin-5-one,
2-[3-(1H-Tetrazol-5-yl)-phenylethynyl]-7,8-dihydro-6H-quinolin-5-one,
2-[3-Fluoro-5-(1H-tetrazol-5-yl)-phenylethynyl]-6,6-dimethyl-7,8-dihydro-6H-quinolin-5-one,
2-[3-Fluoro-5-(1H-tetrazol-5-yl)-phenylethynyl]-7,7-dimethyl-7,8-dihydro-6H-quinolin-5-one,
2-[3-Fluoro-5-(1H-tetrazol-5-yl)-phenylethynyl]-7,8-dihydro-6H-quinolin-5-one,
2-(3-Trifluoromethyl-phenylethynyl)-7,8-dihydro-6H-quinolin-5-one,
7,7-Dimethyl-2-(3-trifluoromethyl-phenylethynyl)-7,8-dihydro-6H-quinolin-5-one,
6,6-Dimethyl-2-(3-trifluoromethyl-phenylethynyl)-7,8-dihydro-6H-quinolin-5-one,
7,7-Dimethyl-2-phenylethynyl-7,8-dihydro-6H-quinolin-5-one,
6,6-Dimethyl-2-phenylethynyl-7,8-dihydro-6H-quinolin-5-one,
2-(4-Methyl-thiazol-2-ylethynyl)-7,8-dihydro-6H-quinolin-5-one,
7,7-Dimethyl-2-(4-methyl-thiazol-2-ylethynyl)-7,8-dihydro-6H-quinolin-5-one,
6,6-Dimethyl-2-(4-methyl-thiazol-2-ylethynyl)-7,8-dihydro-6H-quinolin-5-one,
2-(4-Fluoro-thiazol-2-ylethynyl)-7,8-dihydro-6H-quinolin-5-one,
2-(4-Fluoro-thiazol-2-ylethynyl)-7,7-dimethyl-7,8-dihydro-6H-quinolin-5-one,
2-(4-Fluoro-thiazol-2-ylethynyl)-6,6-dimethyl-7,8-dihydro-6H-quinolin-5-one,
2-(2-Phenyl-oxazol-5-ylethynyl)-7,8-dihydro-6H-quinolin-5-one,
2-(2-Phenyl-thiazol-5-ylethynyl)-7,8-dihydro-6H-quinolin-5-one,
2-(5-Fluoro-pyridin-3-ylethynyl)-7,8-dihydro-6H-quinolin-5-one,
3-Fluoro-5-(7,7-Dimethyl-5-oxo-5,6,7,8-tetrahydro-quinolin-2-ylethynyl)-benzonitrile,
2-(4-Fluoro-5-phenyl-oxazol-2-ylethynyl)-7,8-dihydro-6H-quinolin-5-one,
2-(4-Fluoro-5-pyridin-3-yl-oxazol-2-ylethynyl)-7,8-dihydro-6H-quinolin-5-one,
2-(4-Fluoro-5-pyridin-3-yl-oxazol-2-ylethynyl)-7,7-dimethyl-7,8-dihydro-6H-quinolin-5-one,
2-(4-Fluoro-5-pyridin-3-yl-oxazol-2-ylethynyl)-6,6-dimethyl-7,8-dihydro-6H-quinolin-5-one,
6,6-Dimethyl-2-pyridin-2-ylethynyl-7,8-dihydro-6H-quinolin-5-one,
6,6-Dimethyl-2-(4-methyl-oxazol-2-ylethynyl)-7,8-dihydro-6H-quinolin-5-one,
7,7-Dimethyl-2-(4-methyl-oxazol-2-ylethynyl)-7,8-dihydro-6H-quinolin-5-one,
2-(4-Fluoro-5-pyridin-3-yl-1H-imidazol-2-ylethynyl)-7,8-dihydro-6H-quinolin-5-one,
2-(4-Fluoro-5-pyridin-3-yl-1H-imidazol-2-ylethynyl)-7,7-dimethyl-7,8-dihydro-6H-quinolin-5-one,
2-(4-Fluoro-5-pyridin-3-yl-1H-imidazol-2-ylethynyl)-6,6-dimethyl-7,8-dihydro-6H-quinolin-5-one,
6,6-Dimethyl-2-(4-pyridin-3-yl-imidazol-1-ylethynyl)-7,8-dihydro-6H-quinolin-5-one,
7,7-Dimethyl-2-(4-pyridin-3-yl-imidazol-1-ylethynyl)-7,8-dihydro-6H-quinolin-5-one,
2-(4-Pyridin-3-yl-imidazol-1-ylethynyl)-7,8-dihydro-6H-quinolin-5-one,
2-Thiazol-2-ylethynyl-7,8-dihydro-6H-quinolin-5-one,
2-[1,3,4]Thiadiazol-2-ylethynyl-7,8-dihydro-6H-quinolin-5-one,
2-[1,3,4]Oxadiazol-2-ylethynyl-7,8-dihydro-6H-quinolin-5-one,
2-(1H-Tetrazol-5-ylethynyl)-7,8-dihydro-6H-quinolin-5-one,
6,6-Dimethyl-2-[1,3,4]thiadiazol-2-ylethynyl-7,8-dihydro-6H-quinolin-5-one,
7,7-Dimethyl-2-[1,3,4]thiadiazol-2-ylethynyl-7,8-dihydro-6H-quinolin-5-one,
7,7-Dimethyl-2-(1H-tetrazol-5-ylethynyl)-7,8-dihydro-6H-quinolin-5-one,
6,6-Dimethyl-2-(1H-tetrazol-5-ylethynyl)-7,8-dihydro-6H-quinolin-5-one,
6,6-Dimethyl-2-oxazol-5-ylethynyl-7,8-dihydro-6H-quinolin-5-one,
2-Oxazol-2-ylethynyl-7,8-dihydro-6H-quinolin-5-one,
6,6-Dimethyl-2-oxazol-2-ylethynyl-7,8-dihydro-6H-quinolin-5-one,
7,7-Dimethyl-2-oxazol-2-ylethynyl-7,8-dihydro-6H-quinolin-5-one,
6,6-Dimethyl-2-m-tolylethynyl-7,8-dihydro-6H-quinolin-5-one,
7,7-Dimethyl-2-(2-phenyl-oxazol-5-ylethynyl)-7,8-dihydro-6H-quinolin-5-one,
6,6-Dimethyl-2-(2-phenyl-oxazol-5-ylethynyl)-7,8-dihydro-6H-quinolin-5-one,
7,7-Dimethyl-2-(5-phenyl-thiazol-2-ylethynyl)-7,8-dihydro-6H-quinolin-5-one,
6,6-Dimethyl-2-(5-phenyl-thiazol-2-ylethynyl)-7,8-dihydro-6H-quinolin-5-one, 2-(5-Fluoro-pyridin-3-ylethynyl)-7,7-dimethyl-7,8-dihydro-6H-quinolin-5-one, 2-(5-Fluoro-pyridin-3-ylethynyl)-6,6-dimethyl-7,8-dihydro-6H-quinolin-5-one, 3-Fluoro-5-(5-oxo-5,6,7,8-tetrahydro-quinolin-2-ylethynyl)-benzonitrile, 3-(6,6-Dimethyl-5-oxo-5,6,7,8-tetrahydro-quinolin-2-ylethynyl)-5-fluoro-benzonitrile, 2-(4-Fluoro-5-phenyl-oxazol-2-ylethynyl)-7,7-dimethyl-7,8-dihydro-6H-quinolin-5-one, 2-(4-Fluoro-5-phenyl-oxazol-2-ylethynyl)-6,6-dimethyl-7,8-dihydro-6H-quinolin-5-one, 6,6-Dimethyl-2-(5-pyridin-3-yl-[1,3,4]oxadiazol-2-ylethynyl)-7,8-dihydro-6H-quinolin-5-one, 7,7-Dimethyl-2-(5-pyridin-3-yl-[1,3,4]oxadiazol-2-ylethynyl)-7,8-dihydro-6H-quinolin-5-one, and 2-(5-Pyridin-3-yl-[1,3,4]oxadiazol-2-ylethynyl)-7,8-dihydro-6H-quinolin-5-one;

and optical isomers and pharmaceutically acceptable salts thereof.

9. A method for treating a condition selected from: Alzheimer's disease, Huntington's disease, Head and spinal cord injuires/trauma, stroke, convulsions, nicotine addiction, alcohol addiction, opiate addiction, cocaine addiction, anxiety, epilepsy, major depressive disorder, depression, dyskinesia, L-Dopa-induced dyskinesia, migraine, pain, gastroesophageal reflux disease (GERD) and generalized anxiety disorder, in a subject in need thereof, comprising administering a therapeutically effective amount of a compound of claim 1.

10. The method of claim 9, wherein the condition is selected from addiction, L-Dopa-induced dyskinesias, anxiety and epilepsy.

11. A pharmaceutical composition comprising as active ingredient a compound of claim 1 together with one or more pharmaceutically acceptable excipients or vehicles.

* * * * *